(12) United States Patent
Korsmeyer et al.

(10) Patent No.: US 7,868,133 B2
(45) Date of Patent: Jan. 11, 2011

(54) BH3 PEPTIDES AND METHOD OF USE THEREOF

(75) Inventors: Stanley J. Korsmeyer, Weston, MA (US); Anthony Letai, Medfield, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 514 days.

(21) Appl. No.: 11/789,557

(22) Filed: Apr. 24, 2007

(65) Prior Publication Data

US 2008/0234201 A1 Sep. 25, 2008

Related U.S. Application Data

(63) Continuation of application No. 10/658,028, filed on Sep. 9, 2003, now abandoned.

(60) Provisional application No. 60/409,488, filed on Sep. 9, 2002, provisional application No. 60/495,036, filed on Aug. 14, 2003.

(51) Int. Cl.
 C07K 5/00 (2006.01)
 A61K 39/00 (2006.01)
 A61K 38/00 (2006.01)
(52) U.S. Cl. .................. 530/300; 514/2; 424/184.1
(58) Field of Classification Search ............... None
 See application file for complete search history.

(56) References Cited

U.S. PATENT DOCUMENTS

| | | | | |
|---|---|---|---|---|
| 4,522,811 | A | 6/1985 | Eppstein et al. ............... 514/2 |
| 4,676,980 | A | 6/1987 | Segal et al. ................... 424/85 |
| 4,816,567 | A | 3/1989 | Cabilly et al. ................. 530/387 |
| 4,946,778 | A | 8/1990 | Ladner et al. ............... 435/69.6 |
| 5,225,539 | A | 7/1993 | Winter ..................... 530/387.3 |
| 5,545,806 | A | 8/1996 | Lonberg et al. ................. 800/2 |
| 5,545,807 | A | 8/1996 | Surani et al. ................... 800/2 |
| 5,569,825 | A | 10/1996 | Lonberg et al. ................. 800/2 |
| 5,625,126 | A | 4/1997 | Lonberg et al. ................. 800/2 |
| 5,633,425 | A | 5/1997 | Lonberg et al. ................. 800/2 |
| 5,661,016 | A | 8/1997 | Lonberg et al. ............. 435/172.3 |
| 5,916,771 | A | 6/1999 | Hori et al. .................. 435/69.6 |
| 5,939,598 | A | 8/1999 | Kucherlapati et al. ......... 800/25 |
| 5,965,703 | A | 10/1999 | Horne et al. ................. 530/350 |
| 2002/0115613 | A1 | 8/2002 | Kumar ........................ 514/12 |
| 2004/0171809 | A1 | 9/2004 | Korsmeyer et al. .......... 530/350 |

FOREIGN PATENT DOCUMENTS

| | | |
|---|---|---|
| WO | WO 91/00360 | 1/1991 |
| WO | WO 92/20373 | 11/1992 |
| WO | WO 93/08829 | 5/1993 |
| WO | WO 94/02602 | 2/1994 |
| WO | WO 94/11026 | 5/1994 |
| WO | WO 96/27011 | 9/1996 |
| WO | WO 96/33735 | 10/1996 |
| WO | WO 96/34096 | 10/1996 |
| WO | WO 99/53049 | 10/1999 |
| WO | WO 00/59526 | 10/2000 |
| WO | WO 01/12661 A2 | 2/2001 |
| WO | WO 02/20568 | 3/2002 |

OTHER PUBLICATIONS

Oda et al , Science, vol. 288, p. 1053-1058, 2000.*
Matsushita et al , J Neuroscience, vol. 21, p. 6000-7, 2001.*
Sequence search result.*
Adams, et al., *Science*, 281(5381):1322-1326 (1998).
Boyd, et al., *Oncogene*, 11(9):1921-1928 (1995).
Cheng, et al., *Mol. Cell*, 8(3):705-711 (2001).
Chittenden, et al., *EMBO J.*, 14(22):5589-5596 (1995).
Cosulich, et al., *Curr. Biol.*, 7(12):913-920 (1997).
Ellerby, et al., *Nat. Med.*, 5(9):1032-1038 (1999).
Eskes, et al., *Mol. Cell. Biol.*, 20(3):929-935 (2000).
Griffiths, et al., *J. Cell Biol.*, 144(5):903-914 (1999).
Gross, et al., *EMBO J.*, 17(14):3878-3885 (1998).
Holinger, et al, *J. Biol. Chem.*, 274(19):13298-13304 (1999).
Kelekar, et al., *Trends in Cell Biol.*, 8:324-330 (1998).
La Vieira, et al., *Oncogene*, 21(13):1963-1977 (2002).
Li, et al., *Cell*, 94(4):491-501 (1998).
Li, et al., *Nature*, 412:95-99 (2001).
Luo, et al., *Cell*, 94(4):481-490 (1998).
Later, et al., *BMC Cell Biology*, 2:22 (2001).
Matsuzaki, K., *Biochem. Soc. Transactions*, 29:598-601 (2001).
Narita, et al., *Proc. Natl. Acad. Sci. USA*, 95:14681-14686 (1998).
O'Connor, et al., *EMBO J.*, 17(2):384-395 (1998).
Oda, et al., *Science*, 288(5468):1053-1058 (2000).
Polster, et al., *J. Biol. Chem.*, 276(41):37887-37894 (2001).
Putcha, et al., *Neuron*, 29(3):615-628 (2001).
Rothbard, et al., *Nat. Med.*, 6(11):1253-1257 (2000).
Sattler, et al., *Science*, 275:983-986 (1997).
Schimmer, et al., *Cell Death and Differentiation*, 8(7):725-733 (2001).
Terradillos, et al., *FEBS Lett.*, 522(1-3):29-34 (2002).
Wang, et al., *Genes & Development*, 10(22):2859-2869 (1996).
Wang, et al., *Cancer Res.*, 60:1498-1502 (2000).
Wei, et al., *Genes & Development*, 14:2060-2071 (2000).
Wei, et al., *Science*, 292(5517):727-730 (2001).

(Continued)

*Primary Examiner*—Misook Yu
*Assistant Examiner*—Lei Yao
(74) *Attorney, Agent, or Firm*—Mintz Levin Cohn Ferris Glovsky and Popeo, P.C.; Ivor R. Elrifi; Cynthia A. Kozakiewicz

(57) ABSTRACT

The invention provides peptides and the nucleic acid sequences that encode them. The invention further provides therapeutic, diagnostic and research methods for diagnosis, treatment, and prevention of apoptosis associated disorders.

6 Claims, 17 Drawing Sheets

OTHER PUBLICATIONS

Westerhoff, et al., *Proc. Natl. Acad. Sci. USA*, 86(17):6597-6601 (1989).
Wolter, et al., *J. Cell Biol.*, 139(5):1281-1292 (1997).
Yang, et al., *Cell*, 80(2):285-291 (1995).
Yang, et al., *Methods Enzymol.*, 130:208-269 (1986).
Zha, et al., *J. Biol. Chem.*, 272(39):24101-24104 (1997).
Zha, et al., *Science*, 290(5497)1761-1765 (2000).
Zong, et al., *Genes & Development*, 15:1481-1486 (2001).
Aït-Ikhlef et al. *Neurosci. Lett.*, 199:163-166 (1995).
International Search Report for PCT/US03/28482, mailed Dec. 8, 2005.
Werner et al., "Bcl-2 Family Member Bfl-1/A1 Sequesters Truncated Bid to Inhibit its Collaboration With Pro-Apoptotic Bak or Bax". *J. Biol. Chem.*,277(25):22781-22788 (2002).
Supplementary Partial European Search Report for EP 03 74 9602, mailed Sep. 28, 2006.
Brady et al., "Reflections on a peptide" *Nature*, 368:692-693 (1994).
Brennan et al., "Preparation of Bispecific Antibodies by Chemical Recombination of Monoclonal Immunoglobulin $G_1$ Fragments" *Science*, 229:81 (1985).
Caron et al., "Engineered Humanized Dimeric Forms of IgG Are More Effective Antibiotics", *J. Exp. Med.*, 176:1191-1195 (1992).
Cole et al., "The EBV-Hybridoma technique and its application to human lung cancer", *Monoclonal Antibodies and Cancer Therapy*, 77-96 (1985).
Cote et al., "Generation of human monoclonal antibiotics reactive with cellular antigens", *Proc. Natl. Acad. Sci. USA*, 80:2026-2030 (1983).
DeGrado, "Designs of peptides and proteins", *Adv Protein Chem*, 39:51-124 (1988).
Fishwild et al., "High-avidity human IgGk monoclonal antibodies from a novel strain of minilocus transgenic mice", *Nature Biotechnology*, 14:845-851 (1996).
Futaki et al., "Arginine-rich Peptides: An Abundant Source of Membrane-Permeable Peptides Having Potential as Carriers for Intracellular Protein Delivery", *J. Biol. Chem.*, 276(8):5836-5840(2001).
Grosschedl et al., "Introduction of a μ immunoglobulin gene into the mouse germ line: specific expression in lymphoid cells and synthesis of functional antibody", *Cell*, 38:647-658 (1984).
Gruber et al., "Efficient Tumor Cell Lysis Mediated by a Bispecific Single Chain Antibody Expressed in *Escherichia coli*", *J. Immunol.*, 152:5368-5374 (1994).
Hanahan et al., "Heritable formation of pancreatic β-cell tumors in transgenic mice expressing recombinant insulin/simian virus 40 oncogenes", *Nature*, 315:115-122 (1985).
Hengartner et al., "*C. elegans* Cell Survival Gene ced-9 Encodes a functional Homolog of the Mammalian Proto-Oncogene bcl-2", *Cell*, 76:665-676 (1994).
Hollinger et al., "Diabodies: Small bivalent and bispecific antibody fragments" *Proc. Natl. Acad. Sci. USA*, 90:6444-6448 (1993).
Hoogenboom et al., "By-passing Immunisation, Human Antibodies from Synthetic Repertoires of Germline $V_H$ Gene segments rearranged in Vitro" *J. Mol. Biol.*, 227:381-388 (1992).
Hopp et al., "Prediction of protein antigenic determinants from amino acid sequences" *Proc. Natl. Acad. Sci. USA*, 78:3824-3828 (1981).
Huse et al., "Generation of a large Combinatorial Library of the Immunoglobulin Repertoire in Phage Lambda" *Science*, 246:1275-1281 (1989).
Jameson et al., "A rationally designed CD4 analogue inhibits experimental allergic encephalomyelitis", *Nature*, 368:744-746 (1994).
Jones et al., *Nature*, "Replacing the complementarily- determining regions in a human antibody with those from a mouse", 321:522-525 (1986).
Kohler et al., "Continuous cultures of fused cells secreting anti-body of predefined specificity", *Nature*, 256:495-497 (1975).
Kostelny et al., "Formation of a Bispecific antibody by the Leucine Zippers", *J. Immunol.*, 148(5):1547-1553 (1992).
Kozbor et al., "The production of monoclonal antibodies from human lymphocytes", *Immunol Today*, 4:72-79 (1983).
Kozbor, "A human hybrid Myeloma for production of human monoclonal antibodies", *J. Immunol.*, 133:3001-3005 (1984).
Krieg, "Mechanisms and applications of immune stimulatory CpG oligodeoxynucleotides", *Biochim Biophys Acta*, 1489(1):107-116 (1999).
Kyte et al., "A Simple Method for displaying the Hydropathic Character of a protein", *J. Mol. Biol.*, 157:105-142 (1982).
Li et al., "*tsg 101*: A novel tumor susceptibility gene isolated by controlled Homozygous functional knockout of Allelic Loci in Mammalian Cells", *Cell*, 85:319-329 (1996).
Lonberg et al., "Antigen-specific human antibodies from mice comprising four distinct genetic modifications", *Nature*, 368:856-859 (1994).
Lonberg et al., "Human Antibodies from Transgenic Mice", *Intern. Rev. Immunol.*, 13:65-93 (1995).
Luo et al., Bid, a Bcl2 interacting protein, mediates cytochrome c release from mitochondria in response to activation of cell surface death receptors, *Cell*, 94(4):481-490 (1998).
Marks et al., "By-passing Immunization human Antibodies from v-gene libraries displayed on phage", *J. Mol. Biol.*, 222:581 (1991).
Marks et al., "By-passing immunization: building high affinity human antibodies by chin shuffling" *Bio/Technology*, 10:779-783 (1992).
Mason et al., "The Hypogonadal mouse: reproductive functions restored by gene therapy", *Science*, 234:1372-1378 (1986).
Milstein et al., "Hybrid hybridomas and their use in immunohistochemistry", *Nature*, 305:537-539 (1983).
Morrison et al., "Success in specification", *Nature*, 368:812-813 (1994).
Munson et al., "LIGAND: A Versatile Computerized Approach for Characterization of Ligand-Binding Systems", *Analytical Biochemistry*, 107:220-239 (1980).
Neuberger et al., "Generating high-avidity human Mabs in mice", *Nature Biotechnology*, 14:826 (1996).
Pinckert et al., "An albumin enhancer located 10 kb upstream functions along with its promoter to direct efficient, liver-specific expression in transgenic mice", *Genes and Dev*, 1:268-276 (1987).
Presta, "Antibody engineering", *Curr. Op. Struct. Biol.*, 2:593-596 (1992).
Raff, "Social controls on cell survival and cell death", *Nature*, 356:397-400 (1992).
Readhead et al., "Expression of a myelin basic protein gene in transgenic shiverer mice: correction of the dysmyelinating phenotype", *Cell*, 48:703-712 (1987).
Riechmann et al., "Reshaping human antibodies for therapy",*Nature*, 332:323-327 (1988).
Rothbard et al., "Conjugation of arginine oligomers to cyclosporine A facilitates topical delivery and inhibition of inflammation", *Nature Med.*, 6(11):1253-1257 (2000).
Samson et al., "A 35 amino acid fragment of leptin inhibits feeding in the rat", *Endocrinology*, 137:5182-5185 (1996).
Shalaby et al., "Development of humanized bispecific antibodies reactive with cytotoxic lymphocytes and tumor cells overexpressing the HER2 protooncogene", *Exp. Med.* 175:217-225 (1992).
Shopes, *J. Immunol.*, "A genetically engineered human IgG mutant with enhanced cytolytic activity", 148:2918-2922 (1992).
Stevenson et al., "A chimeric antibody with dual Fc regions (*bis*FabFc) prepared by manipulations at the IgG hinge", *Anti-Cancer Drug Design*, 3:219-230 (1989).
Suresh et al., "Bispecific Monoclonal Antibodies from Hybrid Hybridomas", *Methods in Enzymology*, 121:210-228 (1986).
Suzuki et al., "Possible Existence of Common Internalization Mechanisms among Arginine-rich Peptides", *J. Biol. Chem.*, 277:2437-2443 (2002).
Traunecker et al., "Bispecific single chain molecules (Janusins) target cytotoxic lymphocytes on HIV infected cells", *EMBO J.*, 10:3655-3659 (1991).
Tutt et al., "Trispecific $F(ab')_3$ derivatives that use cooperative signaling via the TCR/CD3 complex and CD2 to activate and redirect resting cytotoxic T cells", *J. Immunol.*, 147:60 (1991).

Verhoeyen et al., "Reshaping Human Antibodies: Grafting an Antilysozyme Activity", *Science*, 239:1534-1536 (1988).

Vieira et al., "Cell permeable BH3-peptides overcome the cytoprotective effect of Bcl-2 and Bcl-$X_L$", *Oncogene*, 21:1963-1977 (2002).

Vitetta et al., "Redesigning Nature's Poisons to Create Anti-Tumor Reagents", *Science*, 238:1098-1104 (1987).

Wang et al., "Bid: A Novel BH3 Domain-Only Death Agonist", *Genes Dev.*, 10(22):2859-2869 (1996).

Wilkinson, "Immunochemical techniques inspire development of new antibody purification methods", *The Scientist*, 14(8):25-28 (2000).

Wolff et al., "Monoclonal antibody homodimers: Enhanced antitumor activity in Nude Mice", *Cancer Research*, 53:2560-2565 (1993).

Matsushita et al., "A high-efficiency protein transduction system demonstrating the role of PKA in long-lasting long-term potentiation", *J. Neurosci.*, 21(16):6000-6007 (2001).

\* cited by examiner

BH3 PEPTIDES AND METHOD OF USE THEREOF

RELATED APPLICATIONS

This application is a continuation of U.S. Ser. No. 10/658,028, filed Sep. 9, 2003 (now abandoned), which claims priority to U.S. Ser. No. 60/409,488, filed Sep. 9, 2002 and U.S. Ser. No. 60/495,036, filed Aug. 14, 2003, all of which are incorporated herein by reference in their entireties.

STATEMENT AS TO FEDERALLY SPONSORED RESEARCH

This invention was made with U.S. government support under NIH grant CA92625. The government has certain rights in the invention.

FIELD OF THE INVENTION

This invention relates generally to methods and compositions for the regulation of apoptosis.

BACKGROUND OF THE INVENTION

Programmed cell death, referred to as apoptosis, plays an indispensable role in the development and maintenance of tissue homeostasis within all multicellular organisms (Raff, Nature 356: 397-400, 1992). Genetic and molecular analysis from nematodes to humans has indicated that the apoptotic pathway of cellular suicide is highly conserved (Hengartner and Horvitz, Cell 76: 1107-1114, 1994). In addition to being essential for normal development and maintenance, apoptosis is important in the defense against viral infection and in preventing the emergence of cancer.

Diverse intrinsic death signals emanating from multiple subcellular locales all induce the release of cytochrome c from mitochondria to activate Apaf-1 and result in effector caspase activation. Proteins in the BCL-2 family are major regulators of the commitment to programmed cell death as well as executioners of death signals at the mitochondrion. Members of this family include both pro- and anti-apoptotic proteins and share homology in up to four conserved regions termed BCL-2 homology (BH) 1-4 domains (Adams and Cory, 1998). The family can be divided into three main subclasses. The anti-apoptotic proteins, which include BCL-2 and BCL-$X_L$, are all "multidomain," sharing homology throughout all four BH domains. However, the pro-apoptotic proteins can be further subdivided and include multidomain proteins, such as BAX and BAK, which possess sequence homology in BH1-3 domains. The more distantly related "BH3-only" proteins are to date all pro-apoptotic and share sequence homology within the amphipathic α-helical BH3 region, which is required for their apoptotic function (Chittenden et al., 1995; O'Connor et al., 1998; Wang et al., 1996; Zha et al., 1997).

Multidomain pro-apoptotic proteins such as BAX and BAK upon receipt of death signals participate in executing mitochondrial dysfunction. In viable cells, these proteins exist as monomers. In response to a variety of death stimuli, however, inactive BAX, which is located in the cytosol or loosely attached to membranes, inserts deeply into the outer mitochondrial membrane as a homo-oligomerized multimer (Eskes et al., 2000; Gross et al., 1998; Wolter et al., 1997). Inactive BAK resides at the mitochondrion where it also undergoes an allosteric conformational change in response to death signals, which includes homo-oligomerization (Griffiths et al., 1999; Wei et al., 2000). Cells deficient in both BAX and BAK are resistant to a wide variety of death stimuli that emanate from multiple locations within the cell (Wei et al., 2001).

The BH3-only molecules constitute the third subset of this family and include BID, NOXA, PUMA, BIK, BIM and BAD (Kelekar and Thompson, 1998). These proteins share sequence homology only in the amphipathic α-helical BH3 region which mutation analysis indicated is required in pro-apoptotic members for their death activity. Moreover, the BH3-only proteins require this domain to demonstrate binding to "multidomain" BCL-2 family members. Multiple binding assays, including yeast two-hybrid, co-immunoprecipitation from detergent solubilized cell lysates and in-vitro pull down experiments indicate that individual BH3-only molecules display some selectivity for multidomain BCL-2 members (Boyd et al., 1995; O'Connor et al., 1998; Oda et al., 2000; Wang et al., 1996; Yang et al., 1995). The BID protein binds pro-apoptotic BAX and BAK as well as anti-apoptotic BCL-2 and BCL-$X_L$ (Wang et al., 1996; Wei et al., 2000). In contrast, BAD, NOXA and BIM as intact molecules display preferential binding to anti-apoptotic members (Boyd et al., 1995; O'Connor et al., 1998; Oda et al., 2000; Yang et al., 1995).

SUMMARY OF THE INVENTION

The present invention is based on the discovery that the BH3 domain from the BCL-2 family of proteins alone can function as a specific death ligand. The peptides are referred to herein as BH3 peptides.

In one aspect the invention provides an isolated peptide having a sequence of SEQ ID NO: 1, 2 or 10. The peptide induces BAK oligomerization and cytochrome c release from mitochondria. In another aspect the invention provides an isolated peptide having a sequence of SEQ ID NOs: 3-9 or 11. The peptide binds BCL-2 or MCL-1. For example, SEQ ID NO:1-5 binds BCL-2. Alternatively, SEQ ID NO: 6 and 7 bind MCL-1.

Also include in the invention is a chimeric peptide having a first domain and a second domain. The first domain having and amino acid sequence of SEQ ID NOs: 1-11. The second domain having a translocation sequence which facilitates transport across a biological membrane. Examples, of translocation sequence includes polyarginine.

In another aspect the invention includes a nucleic acid encoding any one of the peptides of the invention.

Also included in the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a composition that includes the peptides of the invention and a carrier or diluent.

In yet a further aspect the invention provides methods of treating a cell proliferative disorder, e.g., cancer in a subject by administering to a subject a BH3 peptide.

In another aspect the invention includes a method of inducing apoptosis in a cell by contacting said cell with SEQ ID NOs 1, 2 or 10 such that apoptosis is induced. Alternatively, the invention provides a method of sensitizing a cell to apoptosis by contacting said cell with a composition comprising any of SEQ ID NOs: 3-7 or 11 such that as to sensitize the cell to apoptosis.

A further aspect the invention includes a method of screening for an apoptotic sensitizer compound by contacting mitochondria overexpressing BCL-2 with a BID-like BH3 peptide to form a BCL-2-peptide complex and contacting the complex with a test compound. Cytochrome c release from the mitochondria is determined and compared to Cytochrome c release from the mitochondria not exposed to the compound. An increase of cytochrome c release in the presence of the test compound compared to the absence of the compound indicates the compound is an apoptotic sensitizer compound.

In another aspect, the invention relates to a transgenic animal containing a heterologous gene construct encoding a protein comprising BCL-2 protein, or a cell isolated from this animal. The gene construct is ubiquitously expressed. Alternatively, the gene construct is constitutively expressed. The gene constructs contain one or more regulatory sequences, such as a promoter. For example, the gene construct is under the control of an inducible promoter. The transgenic animal is useful for in vitro testing to determine the effect of a BCL-2 antagonist.

In another aspect, the invention relates to a method of using cell lines isolated from a transgenic animal in an in vitro assay to determine the inhibition of a BCL-2 protein, inhibition of an anti-apoptotic BCL-2 protein family member or determine the effects or antagonist thereof.

In another aspect, the invention relates to a transgenic non-human animal containing a recombinant nucleic acid molecule stably integrated in its genome, where the recombinant nucleic acid molecule encodes a BCL-2 protein.

In a further aspect, the invention relates to a method for the production of a transgenic non-human animal, which includes introduction of a recombinant nucleic acid molecule into a germ cell, an embryonic cell, an egg cell or a cell derived therefrom, where the recombinant nucleic acid molecule encodes a BCL-2 protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
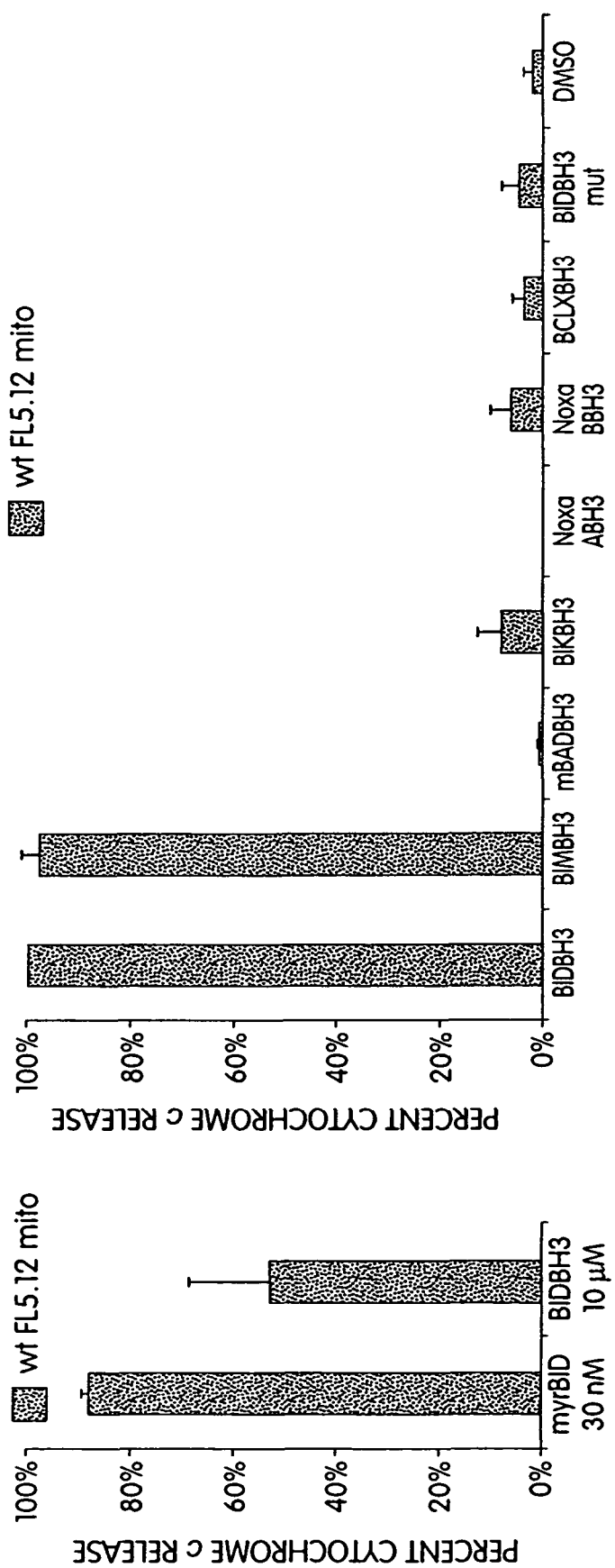
FIGS. 1A and 1B are bar charts showing BIDBH3, myr-BID, and BIMBH3 proteins and peptides induce cytochrome c release from mitochondria.

The present invention is based in part on the discovery that peptides comprising the BH3 domain from the BCL-2 family of proteins can function as a specific death ligand. The peptide of the invention were derived in part from the BH3 domain of BID, BIM, BAD, BIK, NOXA, and BCLX polypeptides and initiate cell death either by activating pro-apoptotic members or by counteracting anti-apoptotic members, by displacing BH3 domains from their pockets. The peptides which activate pro-apoptotic members are referred to herein as "BID-like BH3 peptides" (e.g., SEQ ID NO: 1, 2, and 10) whereas the peptides that counteract anti-apoptotic members, are referred to herein as "BAD-like BH3 peptide" (e.g., SEQ ID NO: 3-7 and 11). The BID-like and BAD-like peptide are summarized below in Table 1 and are collectively referred to herein as BH3 peptides. Additionally, the invention provides methods and pharmaceutical compositions for treating pathophysiologies associated with apoptosis, e.g., cell proliferative disorders.

TABLE 1

| | Amino Acid Sequence | SEQ ID NO | $K_d$(nM), BCL-2 Binding | SD +/- | IC50 (nM), BID Displacement | SD +/- | % Helicity (222 nM) | $K_d$ (nM) MCL-1 Binding | SD (+/-) |
|---|---|---|---|---|---|---|---|---|---|
| BIDBH3 | EDIIRNIARHLAQVGDSMDR | 1 | 220 | 30 | 838 | 192 | 19.5 | 283 | 11 |
| BIMBH3 | MRPEIWIAQELRRIGDEFNA | 2 | 74 | 2 | ND | — | 15.8 | 79 | 4 |
| mBADBH3 | LWAAQRYGRELRRMSDEFEGSFKGL | 3 | 39 | 6 | 173 | 60 | ND | >2600 | |
| BADBH3 | NLWAAQRYGRELRRMSDEFVDSFKK | 4 | 41 | 11 | ND | — | 23.9 | | |
| BIKBH3 | MEGSDALALRLACIGDEMDV | 5 | 485 | 272 | 4920 | 1648 | 8.5 | | |
| NOXAABH3 | AELPPEFAAQLRKIGDKVYC | 6 | >1000 | — | >30,000 | — | 5.1 | 752 | 334 |
| NOXABBH3 | PADLKDECAQLRRIGDKVNL | 7 | >1000 | — | >30,000 | — | 11.6 | 829 | 149 |
| BCLXBH3 | VIPMAAVKQALREAGDEFEL | 8 | >1000 | — | >30,000 | — | 3.9 | | |
| BIDBH3 mut | EDIIRNIARHAAQVGASMDR | 9 | >1000 | — | >30,000 | — | 16.4 | >2600 | |
| BID-like consensus | XXXXXXIAXXLXXXGDXXXX | 10 | | | | | | | |
| BAD-like consensus | XXXXXXXXXXLXXXXDXXXX | 11 | | | | | | | |

BH3 Peptides

In one aspect, the invention provides a BH3 peptide. No particular length is implied by the term "peptide". In some embodiments, the BH3 peptide is less than 195 amino acids in length, e.g., less than or equal to 150, 100, 75, 50, 35, 25 or 15 amino acid in length. For example a BH3 peptide includes the sequence of SEQ ID NO: 1-11. In various embodiments, the BH3 peptide includes the amino acid sequence of SEQ ID NO: 1-2 or 10 where the peptide induces BAK oligomerization and cytochrome c mobilization (e.g., release of cytochrome c from the mitochondria). By BAK oligomerization is meant that the BH3 peptide induces the formation of BAK oligomers, e.g., dimers, trimers, etc. The oligomers are hetero-oligomers. Alternatively, the oligomers are homo-oligomers. In a further embodiment, the BH3 peptide stimulates apoptosis, e.g., programmed cell death. Alternatively the BH3 peptides includes the amino acid sequence of SEQ ID NO: 3-5 or 11, where the peptide binds BCL-2 or other anti-apoptotic members of the BCL-2 family of proteins. Alternatively the BH3 peptides includes the amino acid sequence of SEQ ID NO: 6 or 7, where the peptide binds MCL-1 or other anti-apoptotic members of the BCL-2 family of proteins. (See, Table 1).

Examples of BID-like BH3 peptides include a peptide which includes (in whole or in part) the sequence NH₂—XXXXXXIAXXLXXXGDXXXX—COOH (SEQ ID NO:10). Examples of BAD-like BH3 peptides includes (in whole or in part) the sequence NH₂— XXXXXXXXXX-LXXXXDXXXX—COOH (SEQ ID NO:11). As used herein X may be any amino acid. Alternatively, the BID-like or BAD-like BH3 peptides include at least 5, 6, 7, 8, 9, 15 or more amino acids of SEQ ID NO:10 or SEQ ID NO:11)

The BH3 peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

Alternatively, the BH3 peptides are cyclic peptides. BH3 cyclic peptide are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., Endocrinology, 137: 5182-5185 (1996)), or between two amino acid side chains. See, e.g., DeGrado, Adv Protein Chem, 39: 51-124 (1988).

Preparation of BH3 Peptide

BH3 peptides are easily prepared using modern cloning techniques, or may be synthesized by solid state methods or by site-directed mutagenesis. A BH3 peptide may include dominant negative forms of a polypeptide. In one embodiment, native BH3 peptides can be isolated from cells or tissue sources by an appropriate purification scheme using standard protein purification techniques. In another embodiment, BH3 polypeptides are produced by recombinant DNA techniques. Alternative to recombinant expression, BH3 peptides can be synthesized chemically using standard peptide synthesis techniques.

An "isolated" or "purified" protein or biologically active portion thereof is substantially free of cellular material or other contaminating proteins from the cell or tissue source from which the BH3 peptide is derived, or substantially free from chemical precursors or other chemicals when chemically synthesized. The language "substantially free of cellular material" includes preparations of BH3 peptides in which the protein is separated from cellular components of the cells from which it is isolated or recombinantly produced. In one embodiment, the language "substantially free of cellular material" includes preparations of BH3 peptides having less than about 30% (by dry weight) of non-BH3 peptide (also referred to herein as a "contaminating protein"), more preferably less than about 20% of non-BH3 peptide, still more preferably less than about 10% of non-BH3 peptide, and most preferably less than about 5% non-BH3 peptide. When the BH3 peptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BH3 peptides in which the protein is separated from chemical precursors or other chemicals that are involved in the synthesis of the protein. In one embodiment, the language "substantially free of chemical precursors or other chemicals" includes preparations of BH3 peptides having less than about 30% (by dry weight) of chemical precursors or non-BH3 peptide chemicals, more preferably less than about 20% chemical precursors or non-BH3 peptide chemicals, still more preferably less than about 10% chemical precursors or non-BH3 peptide chemicals, and most preferably less than about 5% chemical precursors or non-BH3 peptide chemicals.

The term "biologically equivalent" is intended to mean that the compositions of the present invention are capable of demonstrating some or all of the same apoptosis modulating effects, i.e., release of cytocrome c or BAK oligomerization although not necessarily to the same degree as the BH3 polypeptide deduced from sequences identified from cDNA libraries of human, rat or mouse origin or produced from recombinant expression symptoms.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BH3 peptides can also include derivatives of BH3 peptides which are intended to include hybrid and modified forms of BH3 peptides including fusion proteins and BH3 peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 peptides. By retaining the biological activity, it is meant that cell death is induced by the BH3 polypeptide, although not necessarily at the same level of potency as that of the naturally-occurring BH3 polypeptide identified for human or mouse and that can be produced, for example, recombinantly. The terms induced and stimulated are used interchangeably throughout the specification.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 polypeptide is replaced with another amino acid residue from the same side chain family. Alternatively, in another embodiment, mutations can be introduced randomly along all or part of a BH3 coding sequence, such as by saturation mutagenesis, and the resultant mutants can be screened to identify mutants that retain activity.

Also included within the meaning of substantially homologous is any BH3 peptide which may be isolated by virtue of cross-reactivity with antibodies to the BH3 peptide described herein or whose encoding nucleotide sequences including genomic DNA, mRNA or cDNA may be isolated through hybridization with the complementary sequence of genomic or subgenomic nucleotide sequences or cDNA of the BH3 peptides herein or fragments thereof.

Chimeric and Fusion Proteins

The invention also provides BH3 chimeric or fusion proteins. As used herein, a BH3 or BID mutein "chimeric protein" or "fusion protein" comprises a BH3 or BID mutein polypeptide operatively linked to a non-BH3 polypeptide. An "BH3 peptide" refers to a polypeptide having an amino acid sequence corresponding to a BH3 peptide whereas a "non-BH3 peptide refers to a polypeptide having an amino acid sequence corresponding to a protein that is not substantially homologous to the BH3 peptide, e.g., a protein that is different from the BH3 peptide and that is derived from the same or a different organism. Within a BH3 peptide the BH3 peptide can correspond to all or a portion of a BH3 peptide. In one embodiment, a BH3 peptide fusion protein comprises at least one biologically active portion of a BH3 peptide. In another embodiment, a BH3 peptide fusion protein comprises at least two biologically active portions of a BH3 peptide. Within the fusion protein, the term "operatively linked" is intended to indicate that the BH3 peptide and the non-BH3 peptide are fused in-frame to each other. The non-BH3 peptide can be fused to the N-terminus or C-terminus of the BH3 peptide.

For example, in on aspect the invention provides a chimeric peptide that include a first domain containing BH3 peptide operably linked to a second domain containing a translocation sequence A "translocation sequence" refers to any sequence of amino acids that directs a peptide in which it is present to a desired cellular destination. For example the translocation sequence is polyarginine. Thus, the translocation sequence can direct or facilitate penetration of the peptide across a biological membrane, e.g., a phospholipid membrane, mitochondrial membrane, or nuclear membrane. For example the translocation sequence directs the peptide from outside the cell, through the plasma membrane, and into the cytoplasm or to a desired location within the cell, e.g., the nucleus, the ribosome, the mitochondria, the ER, a lysosome, or peroxisome. Alternatively, or in addition, the translocation sequence can direct the peptide across a physiological barrier such as the blood-brain barrier, the trans-mucosal barrier, or the hematoencephalic, hematoretinal, gastrointestinal and pulmonary barriers.

Alternatively, a BH3 peptide fusion protein comprises a BH3 peptide operably linked to the extracellular domain of a second protein. Such fusion proteins can be further utilized in screening assays for compounds that modulate BH3 peptide activity (such assays are described in detail below).

In another embodiment, the fusion protein is a GST-BH3 peptide fusion protein in which the BH3 peptide sequences are fused to the C-terminus of the GST (i.e., glutathione S-transferase) sequences. Such fusion proteins can facilitate the purification of recombinant BH3 peptide.

In another embodiment, the fusion protein is a BH3 peptide-immunoglobulin fusion protein in which the BH3 peptide sequences comprising one or more domains are fused to sequences derived from a member of the immunoglobulin protein family. The BH3 peptide-immunoglobulin fusion proteins of the invention can be incorporated into pharmaceutical compositions and administered to a subject to inhibit an interaction between a BH3 peptide ligand and a BH3 peptide on the surface of a cell, to thereby suppress BH3 peptide-mediated signal transduction in vivo. In one nonlimiting example, a contemplated BH3 peptide ligand of the invention is a VHL polypeptide. The BH3 peptide-immunoglobulin fusion proteins can be used to affect the bioavailability of a BH3 peptide cognate ligand. Inhibition of the BID α6 peptide ligand/BH3 peptide interaction may be useful therapeutically for both the treatment of proliferative disorders, as well as modulating (e.g., inducing or inhibiting) cell survival or apoptosis. For example, inhibition of the BH3 peptide ligand/BH3 peptide can be used to various disorders as described herein. Moreover, the BH3 peptide-immunoglobulin fusion proteins of the invention can be used as immunogens to produce anti-BH3 antibodies in a subject, to purify BH3 peptide ligands, and in screening assays to identify molecules that inhibit the interaction of BH3 peptide with a BH3 peptide ligand.

In another embodiment, the fusion protein is a BH3 peptide-basic charged domain fusion protein in which the BH3 peptide sequences comprising one or more domains are fused to a basic peptide domain. The BH3 peptide-basic charged domain fusion proteins of the invention can be incorporated into pharmaceutical compositions and administered to a subject to inhibit an interaction between a BH3 peptide ligand and a BH3 peptide in a cell, to thereby suppress BH3 peptide-mediated signal transduction in vivo. Several examples of biologically active fusion proteins, comprising basic peptide domains, for direct delivery of proteins into human patients in the context of protein therapy are known in the art, including, but not limited to, the human immunodeficiency virus type I (HIV-1) TAT protein, HIV-1 Rev protein, *Drosophila Antennapedia* or HIV-1 octaarginine protein. These basic peptide domains can be arginine-rich. These transducing proteins have been shown to have a membrane permeability and a carrier function for the delivery of proteins to the cytoplasm and nucleus of cells, both in vivo and in vitro. These cells can be mammalian cells (i.e. human cells) (Suzuki et al., J Biol Chem 276: 5836-40, 2001 and Suzuki et al., J Biol Chem 277: 2437-43, 2002).

A BH3 chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A BH3 peptide-encoding nucleic acid can be cloned into such an expression vector such that the fusion moiety is linked in-frame to the BH3 peptide.

BH3 Nucleic Acids

The present invention additionally relates to nucleic acids that encode BH3 peptide. Nucleic acids encoding the BH3 peptides may be obtained by any method known in the art (e.g., by PCR amplification using synthetic primers hybridizable to the 3'- and 5'-termini of the sequence and/or by cloning from a cDNA or genomic library using an oligonucleotide sequence specific for the given gene sequence).

For recombinant expression of one or more BH3 peptides, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can be used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic α-cells (see, e.g., Hanahan, et al., 1985. *Nature* 315: 115-122); (ii) the immunoglobulin gene control region active within lymphoid cells (see, e.g., Grosschedl, et al., 1984. *Cell* 38: 647-658); (iii) the albumin gene control region active within liver (see, e.g., Pinckert, et al., 1987. *Genes and Dev* 1: 268-276; (iv) the myelin basic protein gene control region active within brain oligodendrocyte cells (see, e.g., Readhead, et al., 1987. *Cell* 48: 703-712); and (v) the gonadotropin-releasing hormone gene control region active within the hypothalamus (see, e.g., Mason, et al., 1986. *Science* 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors. A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

Also included in the invention are derivatives, fragments, homologs, analogs and variants of BH3 peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments is less than the length of the corresponding full-length nucleic acid or polypeptide from which the BH3 peptides s, or nucleic acid encoding same, is derived. Derivatives and analogs may be full length or other than full length, if the derivative or analog contains a modified nucleic acid or amino acid. Derivatives or analogs of the BH3 peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

The altered sequences can additionally or alternatively be encoded by polynucleotides that hybridize under stringent conditions with the appropriate strand of the naturally-occurring polynucleotide encoding a polypeptide or peptide from which the BH3 peptide is derived. The variant peptide can be tested for BH3 peptide-binding and modulation of BH3 peptide-mediated activity using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5–20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18-20 hours at 55° C. in the same solution with 5–20×10$^6$ cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5–20× 10$^6$ cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

BH3 Antibodies

Also included in the invention are antibodies to BH3 peptides or fragments thereof. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$, and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain. Reference herein to antibodies includes a reference to all such classes, subclasses and types of human antibody species.

An isolated BH3-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, or amino acid sequences as shown in SEQ ID NOs:1-7, and encompasses an epitope thereof such that an antibody raised against the peptide forms a specific immune complex with the full length protein or with any fragment that contains the epitope. By epitope reference is made to an antigenic determinant of a polypeptide. Typically, epitopes contain hydrophilic amino acids such that the particular region of the polypeptide is located on its surface and likely to be exposed in an aqueous based milieu. Preferably, the antigenic peptide comprises at least 3 amino acid residues in a spatial conformation which is unique to the epitope. Generally, the antigenic peptide comprises at least 5 amino acid residues, or at least 10 amino acid residues, or at least 15 amino acid residues, or at least 20 amino acid residues, or at least 30 amino acid residues. Furthermore, antibodies to a BH3 peptide or fragments thereof can also be raised against oligopeptides that include a conserved region such as the α6 helix domain of BID identified herein.

In certain embodiments of the invention, at least one epitope encompassed by the antigenic peptide is a region of BH3 that is located on the surface of the protein, e.g., a hydrophilic region. A hydrophobicity analysis of the human BH3 sequence will indicate which regions of a BH3 are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose-dicorynomycolate) and CpG dinucleotide motifs (Krieg, A. M. Biochim Biophys Acta 1489(1):107-16, 1999).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.*, 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full-length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein (BID or BID α6).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). Homodimeric antibodies with enhanced anti-tumor activity can also be prepared using heterobifunctional cross-linkers as described in Wolff et al. Cancer Research, 53: 2560-2565 (1993). Alternatively, an antibody can be engineered that has dual Fc regions and can thereby have enhanced complement lysis and ADCC capabilities. See Stevenson et al., Anti-Cancer Drug Design, 3: 219-230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Methods of Modulating Apoptosis

Also included in the invention are methods of inducing apoptosis or sensitizing a cell to apoptosis. By "inducing apoptosis" is meant that that the program cell death is initiated. Apoptosis is measured by methods known in the art, for example apoptosis is measured by annexin V staining.

In one aspect apoptosis is induced in subject in need thereof by administering a BH3 peptide or BH3 chimeric peptide in an amount sufficient to induce apoptosis. The subject can be e.g., any mammal, e.g., a human, a primate, mouse, rat, dog, cat, cow, horse, pig. In various aspects the subject is susceptible to cancer or an autoimmune disorder.

A BH3 peptide or BH3 chimeric peptide is administered with an anti-angiogenic compound. Examples of an anti-angiogenic compound include, but are not limited to, a tyrosine kinase inhibitor, an epidermal-derived growth factor inhibitor, a fibroblast-derived growth factor inhibitor, a platelet-derived growth factor inhibitor, a matrix metalloprotease (MMP) inhibitor, an integrin blocker, interferon alpha, interferon-inducible protein 10, interleukin-12, pentosan polysulfate, a cyclooxygenase inhibitor, a nonsteroidal anti-inflammatory (NSAID), a cyclooxygenase-2 inhibitor, carboxyamidotriazole, tetrahydrocortizol, combretastatin A-4, squalamine, 6-O-chloroacetyl-carbonyl)-fumagillol, thalidomide, angiostatin, endostatin, troponin-1, an antibody to VEGF, platelet factor 4 or thrombospondin.

The BH3 peptide or BH3 chimeric peptide is further administered with an chemotherapeutic compound. Examples of chemotherapeutic compounds include, but are not limited to, paclitaxel, Taxol, lovastatin, minosine, tamoxifen, gemcitabine, 5-fluorouracil (5-FU), methotrexate (MTX), docetaxel, vincristin, vinblastin, nocodazole, teniposide, etoposide, adriamycin, epothilone, navelbine, camptothecin, daunonibicin, dactinomycin, mitoxantrone, amsacrine, epirubicin or idarubicin.

Alternatively, the BH3 peptide or BH3 chimeric peptide is further administered with an antibody, such as polyclonal, monoclonal, humanized, human, bispecific, heteroconjugate, immunoconjugate, chimeric, single chain, $F_{ab}$, $F_{ab'}$, and $F_{(ab)2}$ fragments, and an $F_{ab}$ expression library as described above.

In another aspect, apoptosis is induced in a cell by contacting a cell with a BH3 peptide or BH3 chimeric peptide in an amount sufficient to induce apoptosis. Alternatively, a cell is sensitized to apoptosis by contacting a cell with a BH3 peptide or BH3 chimeric peptide in an amount sufficient to sensitize the cell to apoptosis. The cell population that is exposed to, i.e., contacted with, the BH3 peptide or BH3 chimeric peptide can be any number of cells, i.e., one or more cells, and can be provided in vitro, in vivo, or ex vivo.

Some disease conditions are related to the development of a defective down-regulation of apoptosis in the affected cells. For example, neoplasias result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication. At the same time, they modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions, it would be desirable to promote apoptotic mechanisms.

Methods of Screening for Apoptotic Modulating Compounds

The invention further provides a method of screening for compound that modulate apoptosis, i.e., activators or sensitizers.

In various methods, a apoptotic sensitizer compound is identified by contacting a mitochondrion overexpressing an anti-apoptotic protein, e.g. BCL-2 or BCL-$X_L$ with a BID-like BH3 peptide to form a protein-peptide complex. The complex is contacted with a candidate compound, and cytochrome c release is determined and compared to the amount of cytochrome c release in the test population to a control population that has or has not been exposed to the compound An increase in cytochrome c release presence of the compound as compared to the absence of the compound indicates the compound is an apoptotic sensitizer.

The invention also includes an apoptosis sensitizer identified according to this screening method, and a pharmaceutical composition which includes the apoptosis modulator.

Pharmaceutical Compositions

The compounds, e.g., BH3 peptides BH3 chimeric peptides, nucleic acids encoding BH3 peptides, and BH3 and BH3 antibodies (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BH3 peptide or BH3 peptide encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

Transgenic Animals.

In another aspect, the present invention includes transgenic animals having a heterologous (or exogenous) gene construct or transgene encoding a BCL-2 polypeptide. (e.g., the tet-BCL-2 allele)

The preparation of a transgenic mammal includes introducing a nucleic acid construct that expresses a nucleic acid encoding a BCL-2 polypeptide into an undifferentiated cell type, e.g., an embryonic stem (ES) cell. The ES cell is injected into a mammalian embryo, where it integrates into the developing embryo. The embryo is implanted into a foster mother for the duration of gestation.

Embryonic stem cells are typically selected for their ability to integrate into and become part of the germ line of a developing embryo so as to create germ line transmission of the heterologous gene construct. Thus, any ES cell line that has this capability is suitable for use herein. One mouse strain that is typically used for production of ES cells is the 129J strain. A preferred ES cell line is murine cell line D3 (American Type Culture Collection catalog no. CRL 1934). More preferably, the cell line is RW4. The cells are cultured and prepared for DNA insertion using methods well known in the art, such as those set forth by Robertson (Robertson, In: *Teratocarcinomas and Embryonic Stem Cells: A Practical Approach*, E. J. Robertson, ed., IRL Press, Washington, D.C., 1987.). Insertion of the nucleic acid construct into the ES cells can be accomplished using a variety of methods well known in the art including for example, electroporation, microinjection, and calcium phosphate treatment.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of an heterologous nucleic acid, such as DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g., rats, mice, etc. Preferably, the transgenic animals are mice.

Transgenic animals comprise an heterologous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Figure 10:
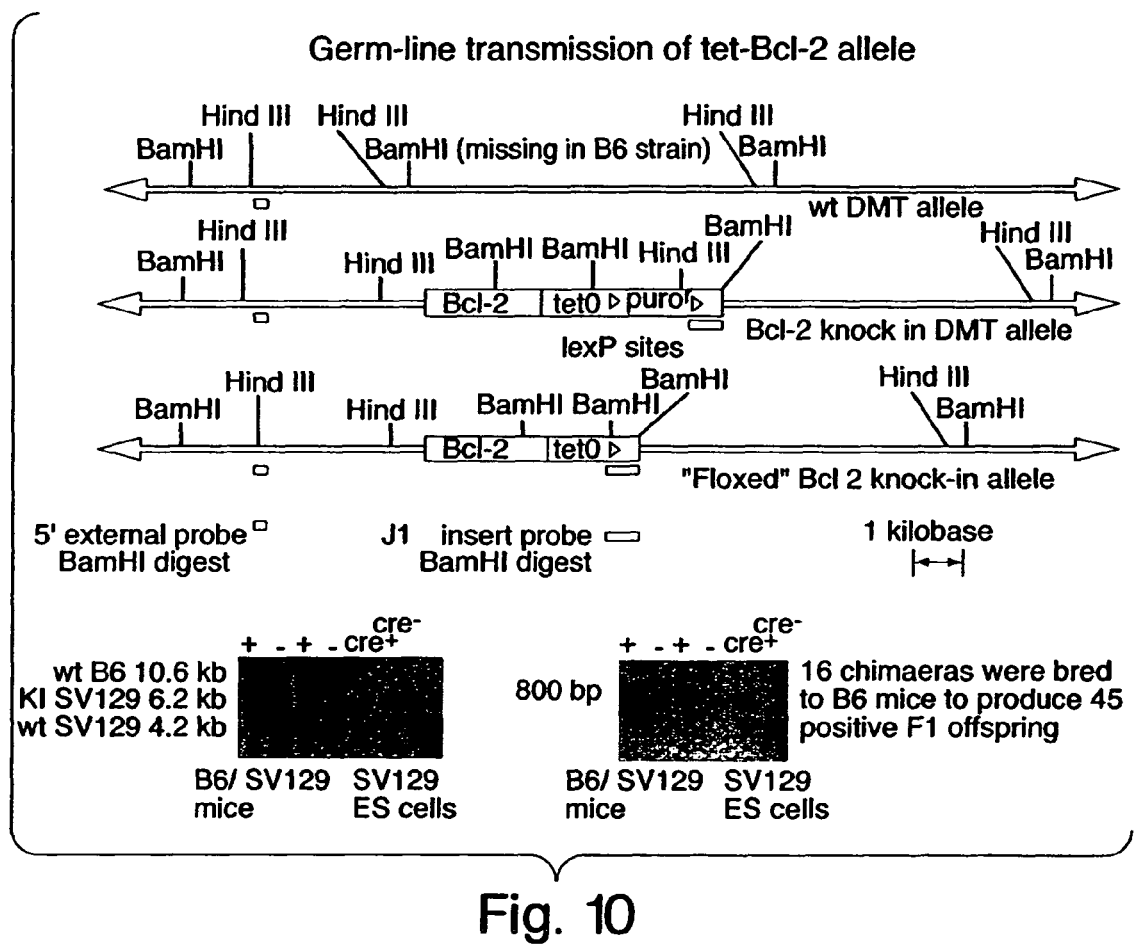
FIG. 10 is a schematic showing the germ-line transmission of tet-Bcl-2 allele.

The heterologous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g., transcriptional activator proteins, are bound to the regulatory sequence(s). The transgenic animals of the invention can comprise other genetic alterations in addition to the presence of the heterologous gene. For example, the host's genome may be altered to affect the function of endogenous genes comprising BH-3 domains (e.g., endogenous BID, BIM, BAD, BIK, NOXA and/or BCLX genes), contain marker genes, or other genetic alterations. Construction of a BCL-2 transgenic mouse is illustrated in FIG. 10 where 16 chimeras were bred to B6 mice to produce 45 positive F1 offspring.

Knockouts and Knockins

Although not necessary to the operability of the invention, the transgenic animals described herein may comprise alterations to endogenous genes comprising BCL-2 in addition to the genetic alterations described above. For example, the host animals may be either "knockouts" and/or "knockins" for a target gene(s) as is consistent with the goals of the invention (e.g., the host animal's endogenous BCL-2 gene may be "knocked out" and/or the BCL-2 gene may be "knocked in"). Knockouts have a partial or complete loss of function in one or both alleles of an endogenous gene comprising BCL-2 genes of interest. Knockins have an introduced transgene with altered genetic sequence and/or function from the endogenous BCL-2 gene. The two may be combined, for example, such that the naturally occurring gene is disabled, and an altered form introduced. For example, it may be desirable to knockout the host animal's endogenous gene comprising BCL-2, while introducing an exogenous gene comprising BCL-2.

In a knockout, preferably the target gene expression is undetectable or insignificant. For example, a knock-out of a gene comprising BCL-2 means that function of the BCL-2 gene has been substantially decreased so that expression is not detectable or only present at insignificant levels. This may be achieved by a variety of mechanisms, including introduction of a disruption of the coding sequence, e.g., insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of BCL-2 genes. A functional knock-out may also be achieved by the introduction of an anti-sense construct that blocks expression of the native genes (See, e.g., Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration post-natally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser. The use of knockin technology may be combined with production of exogenous sequences to produce the transgenic animals of the invention.

The heterologous gene construct includes a nucleic acid encoding a protein comprising BCL-2 proteins. The heterologous gene construct can also encode for various selection markers and enhancer elements.

A selection marker can be any nucleic acid sequence that is detectable and/or assayable. Examples of selection markers include positive selection markers and negative selection markers. Positive selection markers include drug resistance genes; e.g., neomycin resistance genes or hygromycin resistance genes, or beta-galactosidase genes. Negative selection markers, e.g., thymidine kinase gene, diphtheria toxin gene and ganciclovir are useful in the heterologous gene construct in order to eliminate embryonic stem (ES) cells that do not undergo homologous recombination. The selection marker gene is usually operably linked to its own promoter or to another strong promoter from any source that will be active or can easily be activated in the cell into which it is inserted; however, the marker gene need not have its own promoter attached as it may be transcribed using the promoter of the BCL-2 containing gene to be suppressed. In addition, the marker gene will normally have a polyA sequence attached to the 3' end of the gene; this sequence serves to terminate transcription of the gene.

"Enhancer elements" include nucleic acid sequences that are bound by polypeptides associated with transcription, and are usually in cis with the nucleic acid encoding a light-generating fusion protein. Examples of enhancer elements include cyclic AMP response elements (CRE), serum response elements (SRE), nuclear factor B (NF-κB), activator protein 1 (AP-1), serum response factor (SRF), and p53 binding sites. These enhancer elements may further include a TATA box.

The heterologous gene construct may be constitutively expressed in the transgenic mammal. The gene construct may expressed in specific tissues, e.g., the construct is under the control of a tissue-specific promoter.

The invention includes a transgenic mouse containing a heterologous gene construct encoding a BCL-2 protein. The gene construct is under the control of a conditional promoter Activation of the promoter by a transgenic trans-activator protein results in increased expression of the gene construct encoding the BCL-2 protein. Inactivation of the transactivator is achieved by the interaction of a selected biocompatible entity, or parts of the entity, with the transactivator elements. This results in a decrease in expression of the BCL-2 transgene. If the activation occurs only in a part of the animal, only cells in that part will express the BCL-2 proteins.

Transgenic Cell Lines

The invention also includes cell lines derived from the transgenic animals described above. An example cell line is derived from the bone marrow of a triply transgenic (E-mu myc +/tet-Bcl-2 +/MMTVtTA +) leukemic mouse. The cell line is dependent on IL-7 for division. When treated with doxycycline, which turns off BCL-2, all the cells die, demonstrating the BCL-2 dependence of the cell line. The invention also includes a method of using the cell line in an in vitro assay to determine the inhibition of BCL-2 by a peptide or peptidomimetic comprising a BH3 domain (i.e. BCL-2 inhibition) or determine the effects of a test compound (i.e. BH3 agonist).

The invention will be further described in the following examples, which do not limit the scope of the invention described in the claims.

EXAMPLE 1

General Methods

Peptide Stocks

Peptides were synthesized by Tufts University Core Facility, purified by HPLC, and identity confirmed by mass spectroscopy. Stock solutions were 10-20 mM DMSO.

Isolation of Mitochondria

Mouse liver mitochondria were isolated from age-matched wt or Bak −/− mice. Livers were diced, subjected to Dounce rotary Teflon pestle disruption, then homogenized using a Kinematica Polytron homognizer. Following suspension in isolation buffer (250 mM sucrose, 10 mM Tris-HCl pH 7.4, 0.1 mM EGTA), mitochondria were isolated by differential centrifugation steps, followed by two washes in isolation buffer. Mitochondria from FL5.12 cells were isolated by cell disruption followed by differential centrifugation and washing as above. Cell disruption was performed either by a Kinematika Polytron homogenizer or by a combination of Dounce homogenization followed by 6-10 expulsions through a 27 gauge needle.

Cytochrome C Release

Mitochondria at a protein concentration of 0.5 mg/ml were treated at room temperature in experimental buffer (125 mM KCl, 10 mM Tris-MOPS pH 7.4, 5 mM glutamate, 2.5 mM malate, 1 mM KPO$_4$, 10 μM EGTA-Tris pH 7.4). Percent release was quantitated using a colorimetric ELISA (MCTC0, R&D Systems). In all experiments, treatments with DMSO were used as a control for solvent activity.

BMH Cross-Linking 1,6-Bismaleimidohexane was obtained from Pierce (#22330). A 10 mM stock solution in DMSO was added to treated mitochondrial suspensions at a 1:11 dilution. Cross-linking took place for 30 minutes at room temperature, followed by centrifugation to pellet mitochondria. Pellets were dissolved in NuPAGE loading buffer (Invitrogen).

Binding Assays

To determine K$_d$ for peptide binding to BCL-2, a GST-BCL-2 fusion protein lacking the C-terminal transmembrane domain was utilized. Peptides were synthesized with a fluorescein amino-terminus using an AHA linker. Peptides at 25 nM were mixed with titrations of GST-BCL-2 in binding buffer (140 mM NaCL, 10 mM Tris, pH 7.4) at 37° C. An increase in fluorescence polarization measured on a Perkin-Elmer LS 50B luminescence spectrophotometer was quantitated to calculate binding. A non-linear fit to a sigmoidal dose-response curve utilized the program Origin 6.0 to determine K$_d$. For quantitative BIDBH3 displacement assays, 25 nM fluoresceinated BIDBH3 was mixed with 1 μM GST-BCL-2 in binding buffer. Increasing amounts of unlabelled BH3 peptides were titrated in, with loss of fluorescence polarization as a measurement of displacement of BIDBH3. Data were fitted to a sigmoidal curve as above, and IC50 determined.

GST-BCL-2 Production

GST-BCL-2δC21 fusion proteins were induced in BL21 DE3 by 0.1 mM IPTG. The bacterial pellets were resuspended in lysis buffer (1 mg/ml lysozyme/1% Triton X-100/0.1 mg/ml PMSF/2 μg/ml aprotinin/2 μg/ml leupeptine/1 μg/ml pepstatin A in PBS) and sonicated. After centrifugation at 20,000xg for 20 min, the supernatant was applied to glutathione-agarose beads (Sigma). The beads were washed with PBS and treated with 50 mM glutathione/50 mM Tris HCl, pH8.0 to elute protein. Eluate was dialyzed against binding buffer and concentrated using Amicon centrifugal concentrating devices.

Circular Dichroism

Circular dichroism (CD) spectra were obtained on a Jasco J-710 spectropolarimeter at 20° C. using the following standard measurement parameters: wavelength, 190-260 nm; step resolution, 0.5 nm; speed, 20 nm/sec; accumulations, 10; response, 1 sec; band width, 1 nm; path length, 0.1 cm. Stock solutions of peptide were dissolved in deionized water and concentrations determined by amino acid analysis. Samples were then diluted in 50 mM potassium phosphate pH 7 to a calculated final concentration of 50 μM. The CD spectrum of each sample was measured in triplicate and a background spectrum of diluent alone was subtracted. For comparison, the subtracted CD spectra were normalized to 35 μM based on repeat peptide concentration determination by amino acid analysis of the diluted peptide solutions. The α-helical content of each peptide was calculated by dividing the mean residue ellipicity [q]222obs by the reported [q]222obs for a model helical decapeptide (Yang et al., 1986).

Immunoblot Analysis

Antibodies used for immunoblot analysis included anti-cytochrome c (75981A, Pharmingen), anti-BAK (Upstate Biotechnology), and anti-BAX (N-20, Santa Cruz). Antibody detection was accomplished using enhanced chemiluminescence (Western Lightning, Perkin-Elmer).

Jurkat Cell Death

Jurkat cells were grown in RPMI 1640, 10% fetal bovine serum, 100 u/ml penicillin, 100 μg/ml/strep, 2 mM glutamine, 50 μM β-mercaptoethanol. Cells were treated with peptide for 5 hours followed by staining with fluorescently-tagged Annexin V according to manufacturer's protocol (BD Biosciences 556547). Death was quantitated by FACS followed by analysis using FlowJo software (Tree Star, Inc.)

EXAMPLE 2

BH3 Peptides from BID and BIM, But not all BH3-Only Members Release Cytochrome C Similar to Myristoylated Bid Recombinant p15tBID and even more efficiently the p7/myrp15, myristoylated BID complex (myrBID), initiate BAK oligomerization and cytochrome c release in a mitochondrial in-vitro system that appears to recapitulate the mitochondrial pathway of apoptosis in-vivo. Since the pro-apoptotic activity of BID in-vitro and in-vivo requires an intact BH3 domain, we tested the ability of peptides derived from this BH3 domain to initiate this activity. A 20 mer of BIDBH3 (aa 80-99) at 10 μM (Table 1) proved capable of initiating cytochrome c release, as did myrBID (FIG. 1A). the activity of other BH3 domain peptides were compared. While BIMBH3 (Table 1) demonstrated cytochrome c release, peptides derived from other BH3-only members BAD, BIK, and NOXA (Table 1) even at 100 μM did not display this activity (FIG. 1B). A peptide derived from the BH3 domain of anti-apoptotic Bcl-X$_L$ did not cause cytochrome c release (FIG. 1B). Circular dichroism studies indicate that while the relative α-helical content of these peptides varies, the percent α-helicity does not solely dictate the activity of the peptides. While NOXAABH3 and BCL-X$_L$BH3 have relatively low α-helical content, BADBH3 demonstrates the highest α-helical content and is still inactive in this assay (Table 1). Likewise, a peptide derived from the BH3 domain of BID, but containing substitutions (L90A, D95A) at two residues highly conserved throughout the family, retained α-helicity, but did not cause cytochrome c release (Table 1, FIG. 1B).

EXAMPLE 3

BAK is Required for BH3 Peptide-Induced Cytochrome C Release

Figure 2:
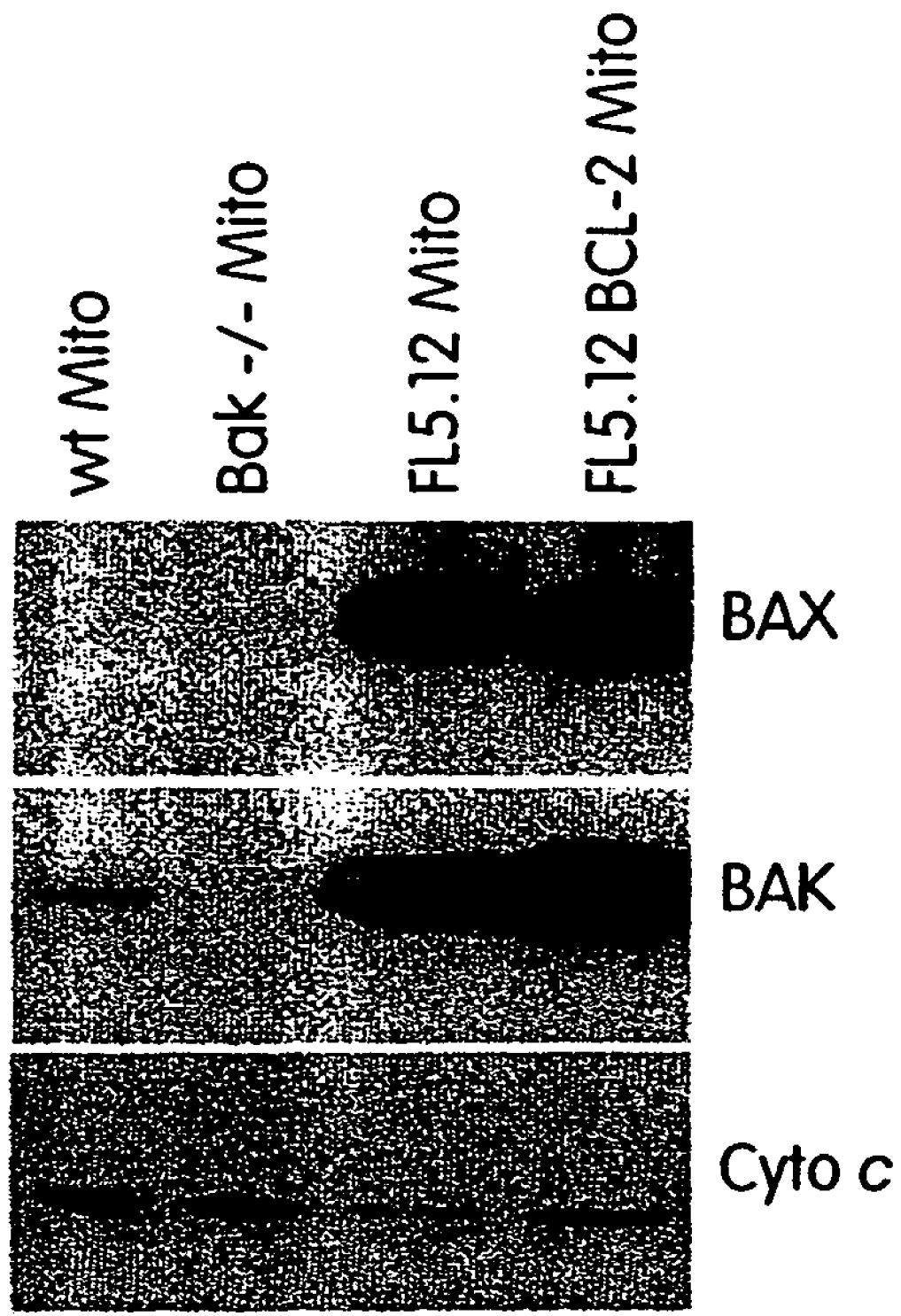
FIG. 2 is a photograph of an immunoblot showing BAX and BAK expression in mitochondria isolated from mouse liver and FL5.12 cells.
Figure 3:
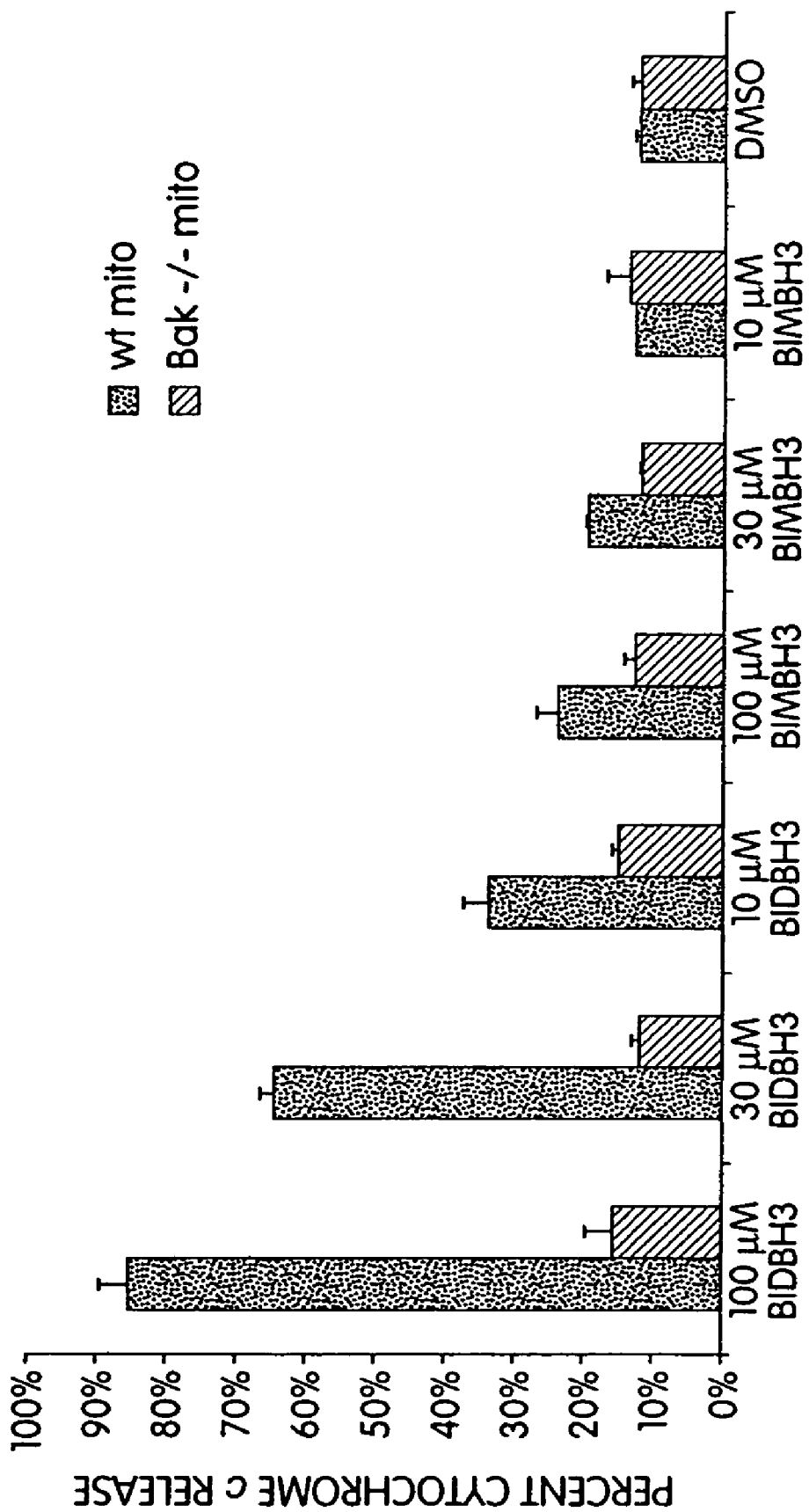
FIG. 3 is a bar chart showing Cytochrome c release induced by BIMBH3 and BIDBH3 is dependent on the presence of the multi-domain pro-apoptotic BAK.

To test whether BH3 peptides work through an established mitochondrial pathway of apoptosis, we examined whether they required the "multidomain" member BAK to be present. One hallmark of cytochrome c release by native tBID is that it requires the presence of multidomain BAK or BAX in intact cells or BAK on purified mitochondria (Wei et al., 2000; Wei et al., 2001). Immunoblots of mitochondria isolated from the liver of Bak −/− mice confirmed that neither "multi-domain" pro-apoptotic BAX nor BAK was present (FIG. 2). Moreover, there is no compensatory alteration in the levels of anti-apoptotic BCL-2 members in the absence of BAX and/or BAK (not shown). Comparison of 100 μM BIMBH3 or BIDBH3 peptide on Bak +/+vs. −/− mitochondria indicated that BAK is required for the release of cytochrome c (FIG. 3). This requirement for BAK argues that these α-helical BH3 peptides function through the genetic pathway of mitochondrial apoptosis rather than by an autonomous permeabilization of membranes which non-specifically damages mitochondria.

EXAMPLE 4

Peptides that Induce Cytochrome C Release Induce BAK Oligomerization

Figure 4A:
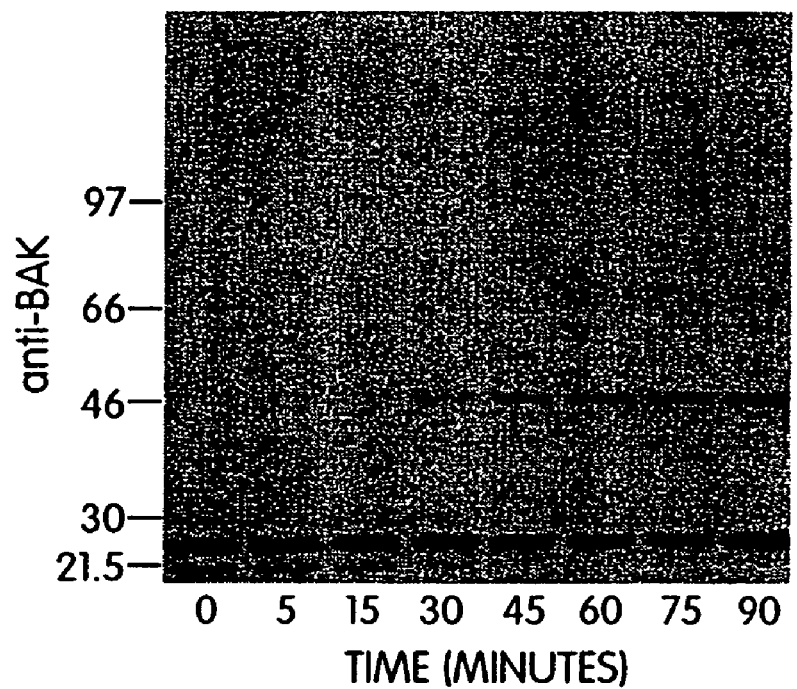
FIG. 4A is an immunoblot showing BAK oligomerization in Wt liver mitochondria treated with 100 μM BIDBH3.
Figure 4B:
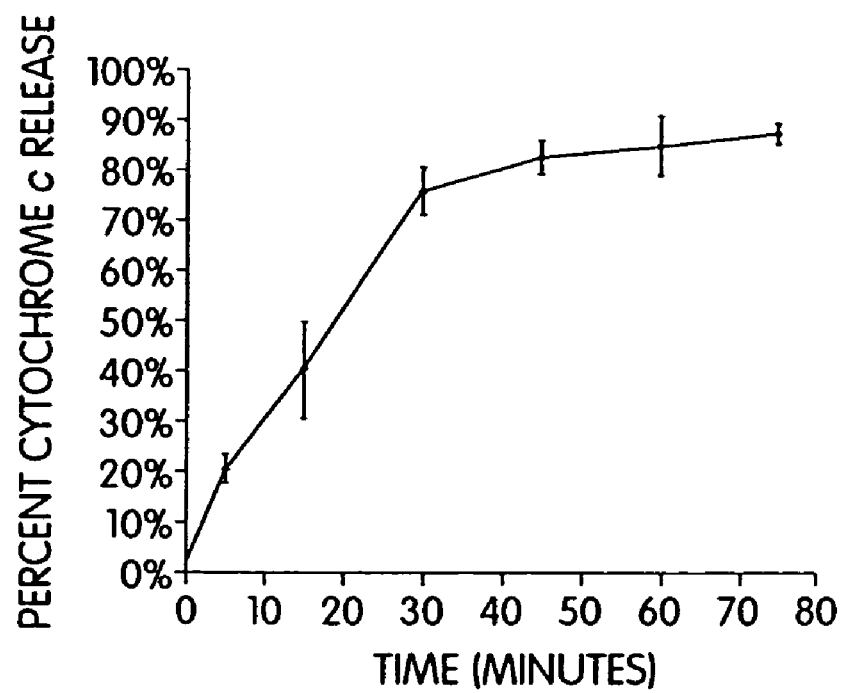
FIG. 4B is a line graph showing peptide induced cytochrome C release. Wt liver mitochondria were treated as in (A) and cytochrome c release measured by ELISA.
Figure 4C:
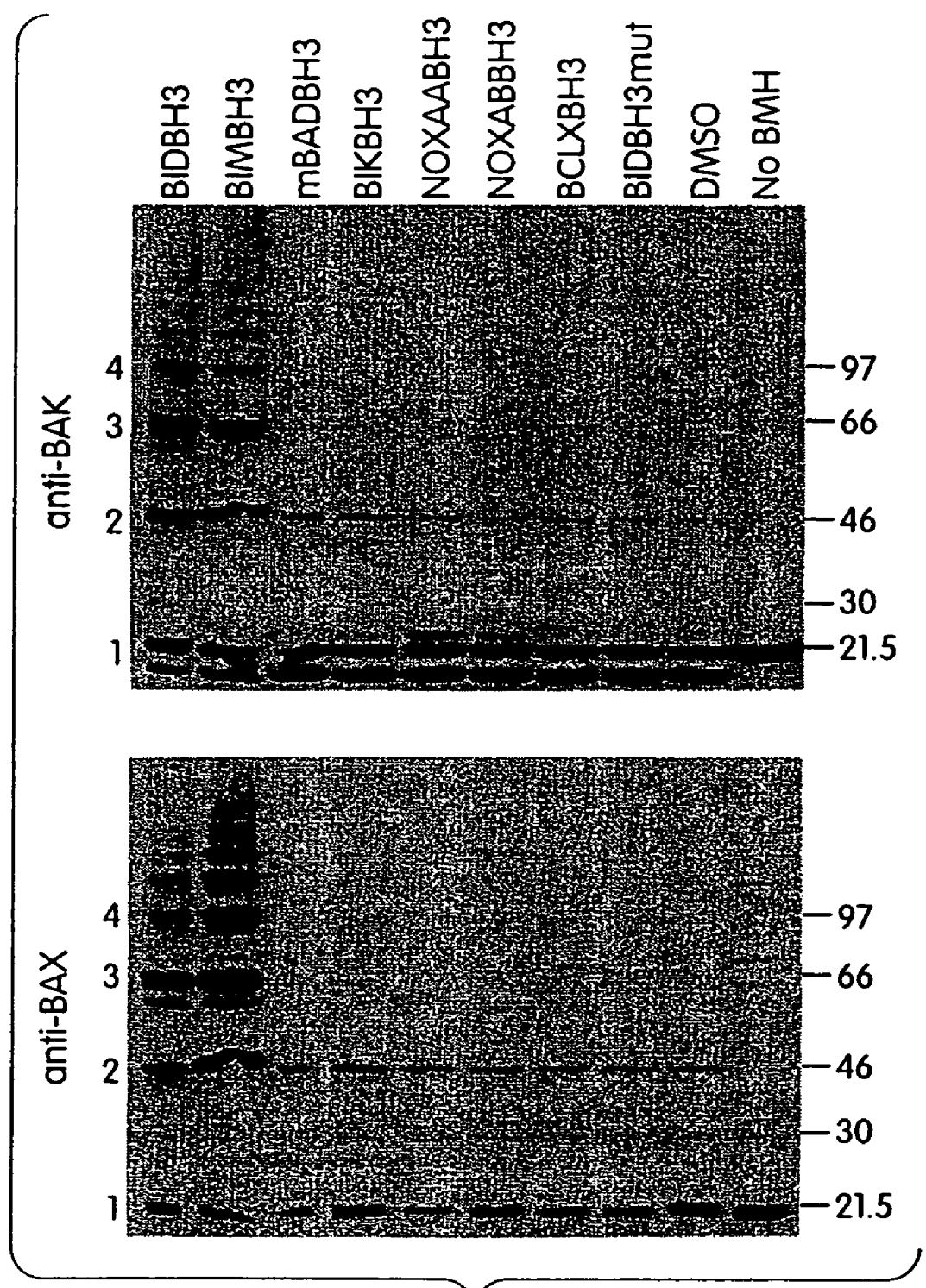
FIG. 4C is a blot showing BAK oligomerization induced by treatment if in mitochondria from FL5.12 cells with 100 μM of the indicated peptides. Markers 1, 2, 3, 4 correspond to size of monomer, dimer, trimer and tetramer.

Previous work demonstrated that the translocation of tBID to the mitochondrion results in allosteric conformational activation of BAK, which includes its homo-oligomerization followed by the release of cytochrome c (Wei et al., 2000). It was found that the BIDBH3 peptide (like tBID or the p7/myr15BID complex) induces BAK oligomerization as detected with the cross-linker, BMH (FIG. 4A). Moreover, there is temporal relationship between BAK oligomerization and the release of cytochrome c induced by BIDBH3 peptide (FIG. 4A,B). While BIMBH3 also induces BAK oligomerization, BADBH3 peptide, which lacks the ability to cause cytochrome c release, is unable to induce BAK oligomerization (FIG. 4C). In was also found that BIMBH3 and BIDBH3, but not BADBH3, could also induce oligomerization of BAX in mitochondria isolated from cultured FL5.12 cells, which contain both BAX and BAK (FIG. 2, 4C). Note that while BIDBH3 induces more prominent cross-linking of BAK than does BIMBH3, BIMBH3 induces more prominent cross-linking of BAX than does BIDBH3. A mutant BID peptide BIDBH3mut (L90A, D95A) was tested and it lacked the ability to induce either cytochrome c release (FIG. 1B) or BAX, BAK oligomerization (FIG. 4C). These results indicate that BIDBH3 and BIMBH3 peptides, like intact tBID protein are capable of inducing an allosteric change in mitochondrial-resident BAK or BAX, which includes their homo-oligomerization and subsequent release of cytochrome c.

EXAMPLE 5

BCL-2 Inhibits Mitochondrial Release of Cytochrome C by BH3 Peptides

Figure 5A:
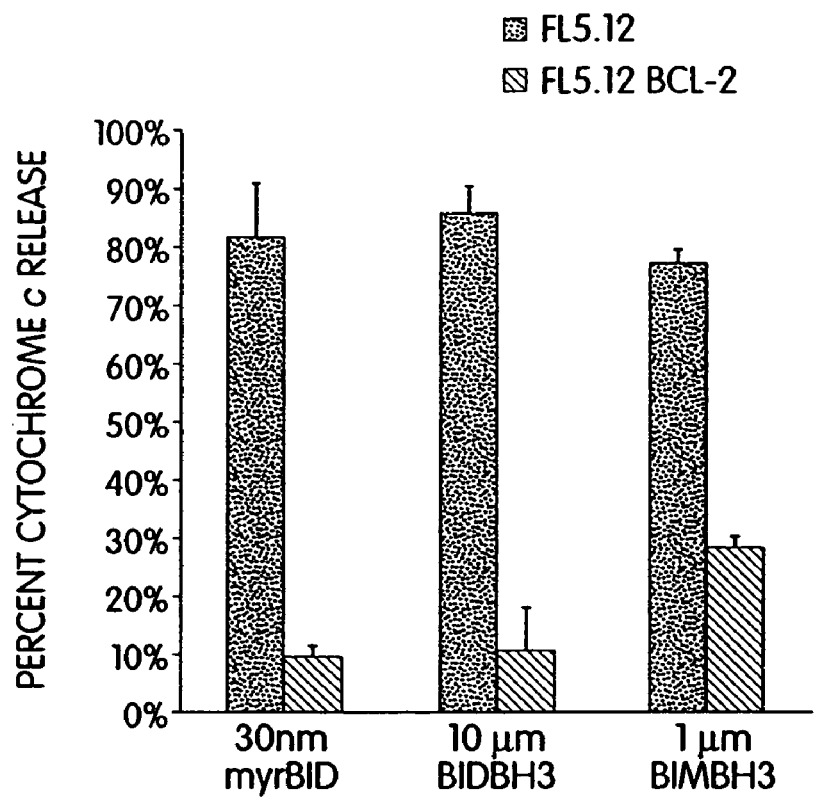
FIG. 5A is a bar chart showing BCL-2 inhibits the release of cytochrome c in mitochondria isolated from parental and BCL-2 over-expressing FL5.12 cells.
Figure 5B:
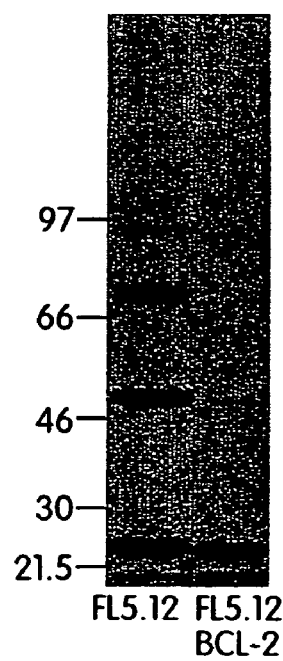
FIG. 5B is a blot showing the oligomerization of BAK in mitochondria from parental and FL5.12-BCL-2 cells treated with 10 μM BIDBH3, incubated with cross-linking agent BMH, and SDS-PAGE and immunoblot for BAK.

Mitochondria bearing protective levels of anti-apoptotic BCL-2 do not release cytochrome c following treatment with 25 ng tBID in vitro, apparently because tBID is bound and sequestered by BCL-2 in stable complexes that prevent tBID from activating BAK (Cheng et al., 2001). Similarly, mitochondria with overexpressed BCL-2 proved resistant to 10 M BIDBH3, 1 μM BIMBH3, as well as 30 nM myrBID failing to release cytochrome c (FIG. 5A) Furthermore, the presence of BCL-2 is coordinate with the loss of BAK oligomerization following exposure to BH3 peptide, suggesting that BCL-2 inhibits upstream of BAK activation (FIG. 5B). These findings support a model wherein a major component of BCL-2's role in inactivating tBID is to specifically sequester the BH3 domain, thus preventing BH3 itself from activating multidomain pro-apoptotic members.

EXAMPLE 6

BADBH3 Binds BCL-2 and Restores Cytochrome C Release by BID

Figure 6A:
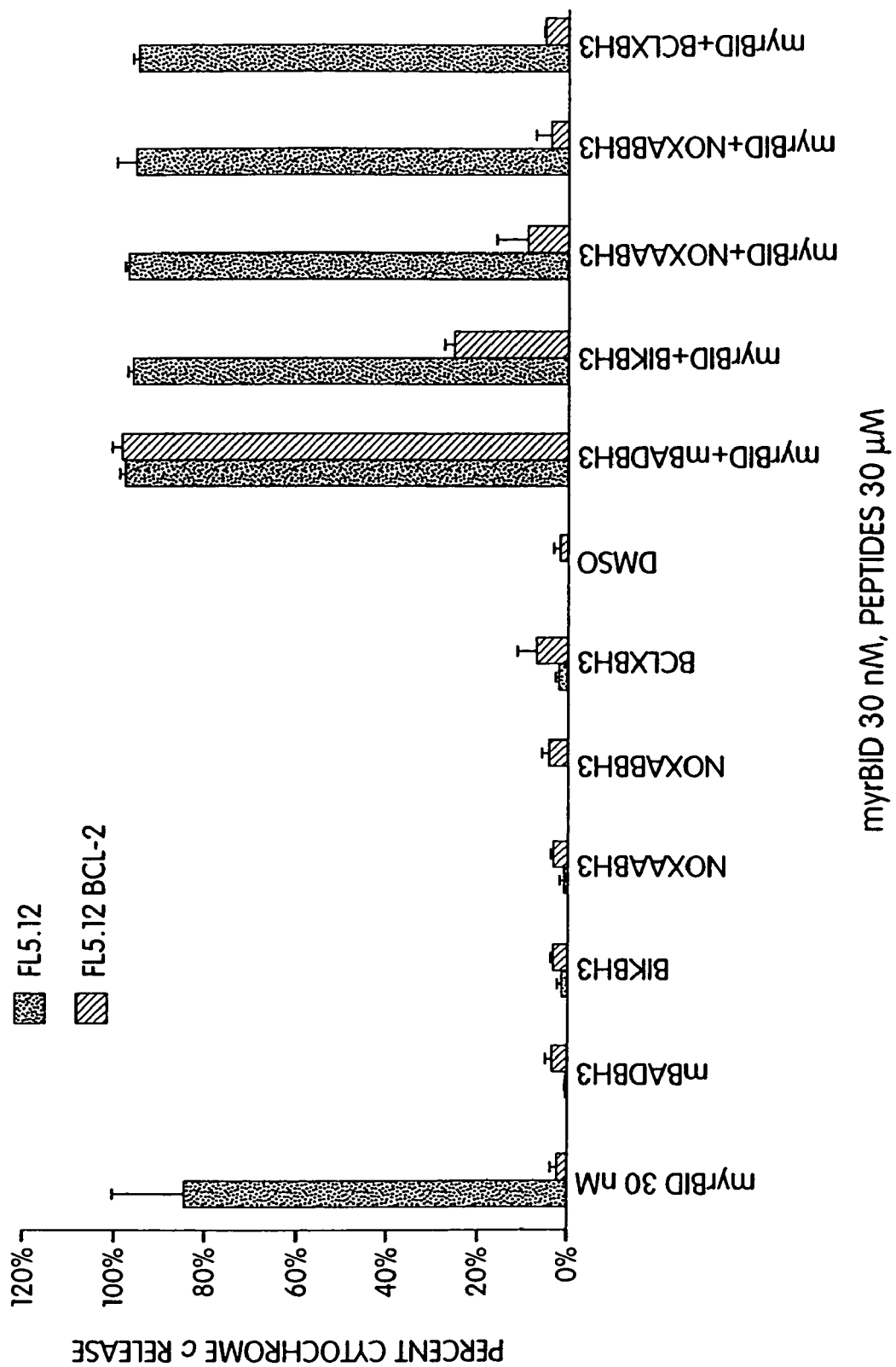
FIG. 6A is a bar chart showing BADBH3 enables cytochrome c release by BIDBH3, BIMBH3 and myrBID.
Figure 6B:
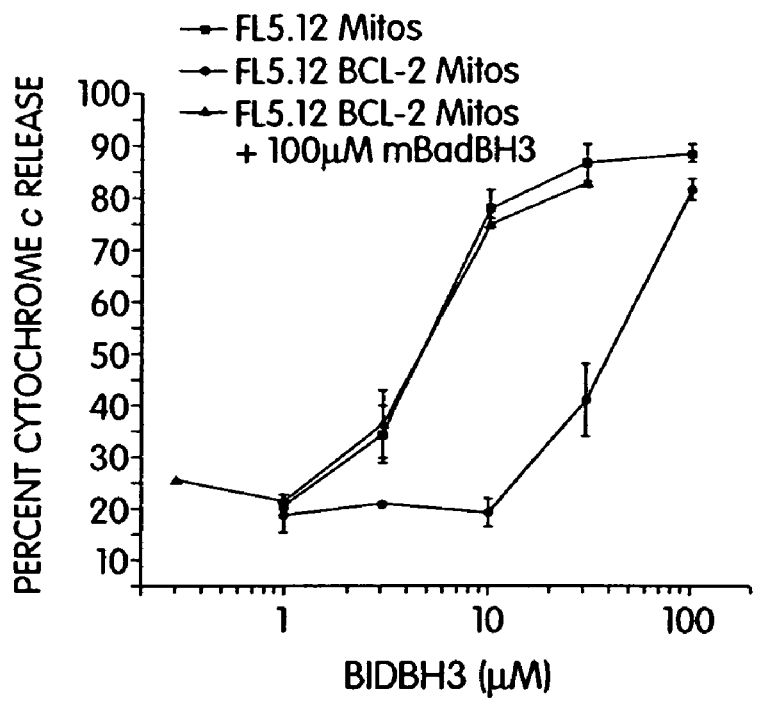
FIG. 6B is a graph showing BADBH3 enables cytochrome c release by BIDBH3 in a dose dependent fashion.
Figure 6C:
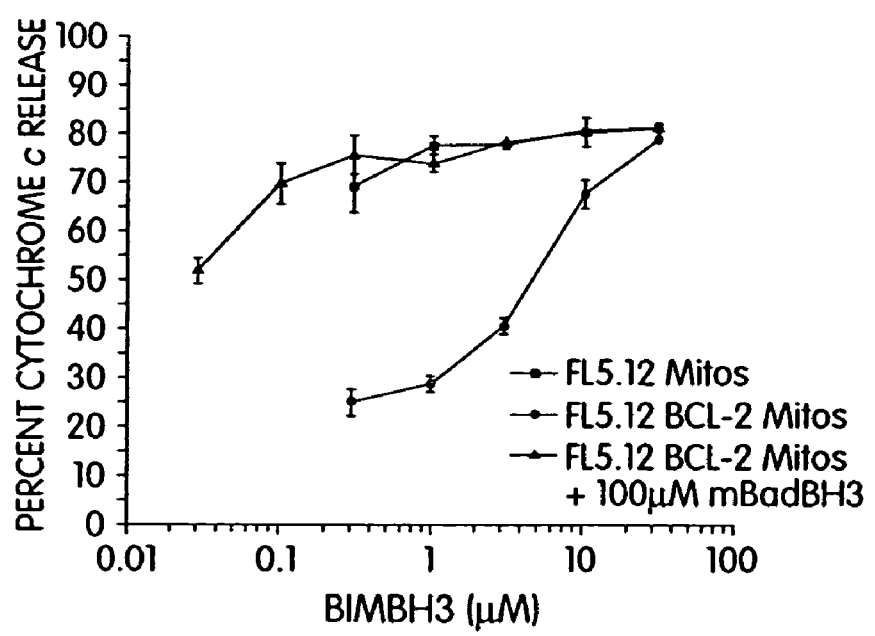
FIG. 6C is a graph showing BADBH3 enables cytochrome c release by BIMDBH3 in a dose dependent fashion.

BH3 peptides were tested which lack the intrinsic ability to activate BAK and cause cytochrome c release for their capacity to interfere with the anti-apoptotic protection by BCL-2. This subset of BH3 peptides might occupy the hydrophobic pocket of BCL-2 and consequently displace proapoptotic BIDBH3 or BIMBH3 peptides. The BADBH3 peptide most prominently demonstrates the capacity to overcome BCL-2 protection of mitochondria treated with a subliminal concentration of myrBID (30 nM), while BIKBH3 shows significant, but lesser, potency (FIG. 6A). The remaining BH3 peptides derived from NOXA and BCL-$X_L$ did not demonstrate the capacity to overcome BCL-2 protection (FIG. 6A). Since even 100 μM BADBH3 in and of itself cannot activate BAK or release cytochrome c, this suggests that BADBH3 sensitizes mitochondria to BIDBH3 or BIMBH3 by successfully competing with these peptides for binding to BCL-2. At 100 μM, BADBH3 was able to restore the cytochrome c release of BCL-2 overexpressing mitochondria in a dose-response fashion to BIDBH3 (FIG. 6B) and BIMBH3 (FIG. 6C) to levels observed for wt mitochondria. An increase in the sensitivity of wt mitochondria treated with BADBH3 was observed. This would be expected, as the source of wt mitochondria, FL5.12 cells, express some murine BCL-2. It was noted that the restoration of cytochrome c release by BADBH3 was accompanied by restoration of BAK oligomerization.

Figure 6D:
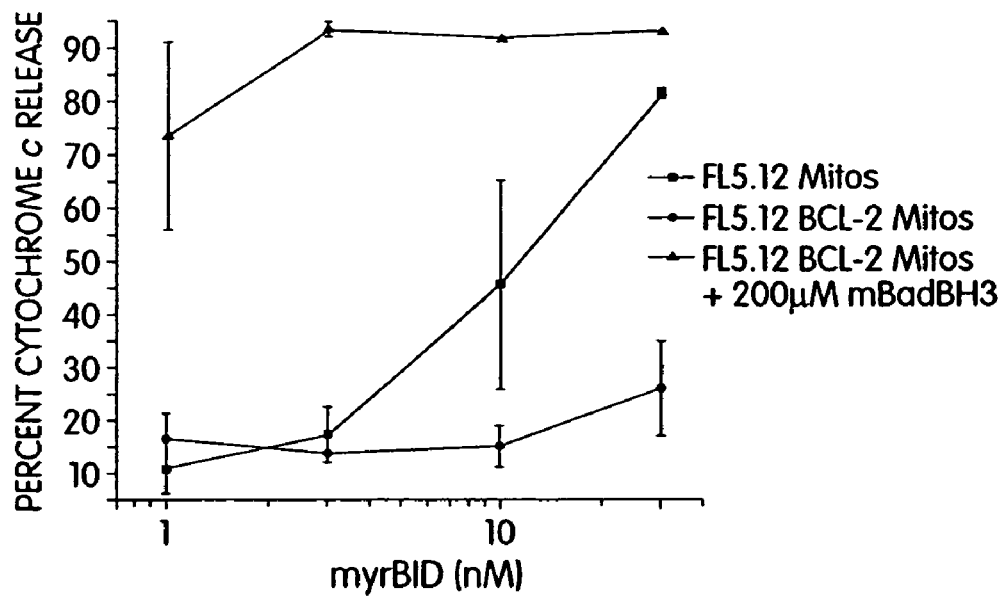
FIG. 6D is a graph showing BADBH3 enables cytochrome c release by myrBID in a dose dependent fashion.
Figure 6E:
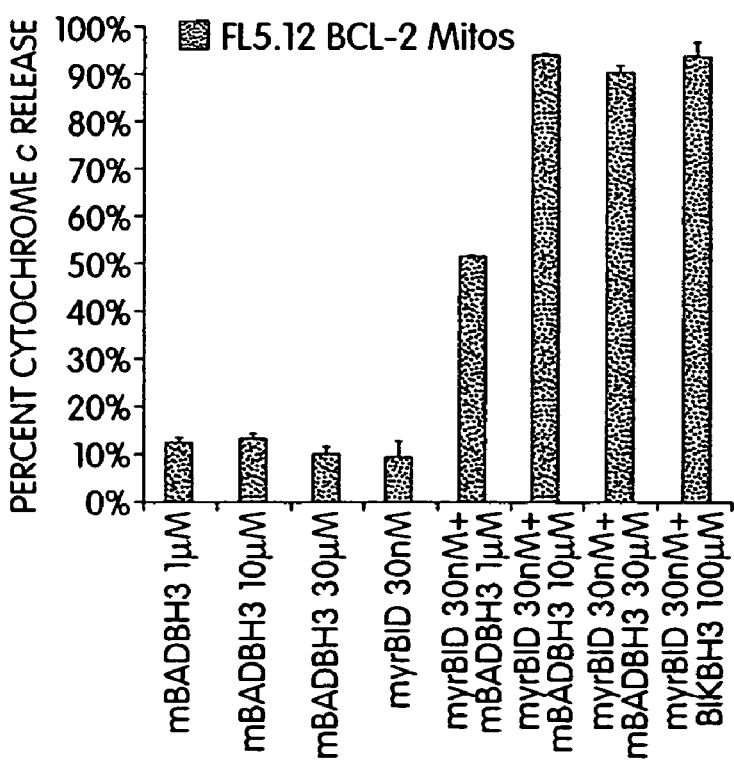
FIG. 6E is bar chart showing the dose response of BADBH3 and BIKBH3 enabling myrBID-induced release of cytochrome c from mitochondria of FL5.12-BCL-2 cells.

Whether eliminating BCL-2 protection by BADBH3 would enable the more physiologic ligand, myristoylated BID complex (p7/myrp15BID) was tested. Addition of 200 μM BADBH3 to BCL-2 overexpressing mitochondria markedly restores their sensitivity to even 1 nM myrBID. These BADBH3 treated mitochondria are more sensitive than wt mitochondria, probably reflecting the capacity of BADBH3 to inhibit the endogenous murine BCL-2 and BCL-$X_L$ resident on the mitochondria (FIG. 6D). The dose response range of BADBH3 was examined, revealing it had measurable activity at concentrations as low as 1 μM in inhibiting BCL-2 (FIG. 6E) and enabling cytochrome c release by myrBID. At 100 μM, BIKBH3 can also restore near-total cytochrome c release to mitochondria over-expressing BCL-2, demonstrating a mechanism of action like BADBH3, albeit at higher concentrations (FIG. 6E). This reveals that short BADBH3 and BIKBH3 peptides can effectively compete with the natural myrBID protein for binding BCL-2 thus abrogating BCL-2's antiapoptotic effect and enabling myrBID induced cytochrome c release.

EXAMPLE 7

BADBH3 Displaces BIDBH3 from BCL-2 by Fluorescence Polarization Analysis

Figure 7A:
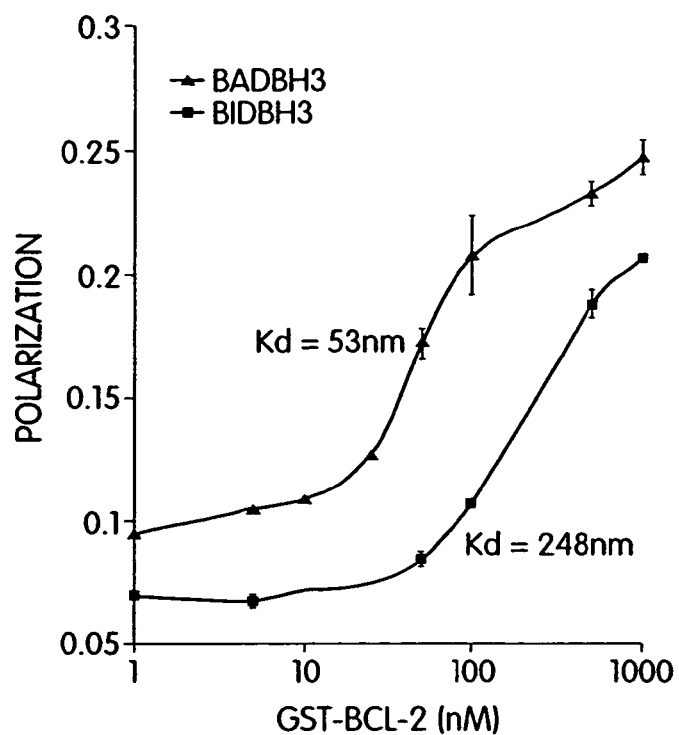
FIG. 7A is a graph showing binding of BIDBH3 and BADBH3 binding to GST-BCL-2
Figure 7B:
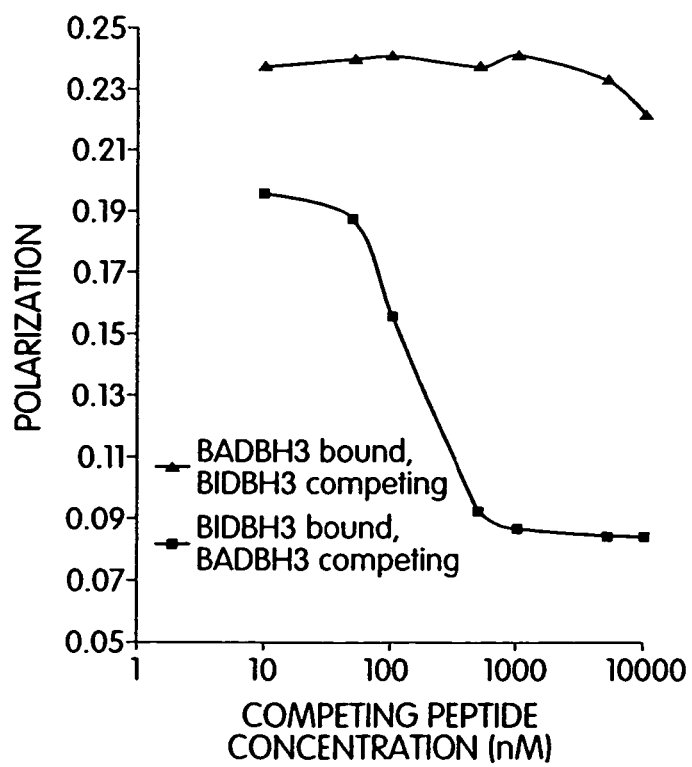
FIG. 7B is a graph showing displacement of BIDBH3 binding to GST-BCL-2 by BADBH3
Figure 7C:
FIG. 7C is a schematic model of the BID-Like domain.
Figure 7D:
FIG. 7D is a is a schematic model of the BAD-Like domain.

To directly test whether BADBH3 could displace BIDBH3 from BCL-2 we utilized fluorescence polarization analysis. BADBH3 peptide bound full-length BCL-2 with approximately 5-fold greater affinity than BIDBH3 peptide (average of 41 vs. 220 nM, Table 1, FIG. 7A). Moreover, BADBH3 can efficiently displace pre-bound BIDBH3 peptide from BCL-2 (FIG. 7B). However, to compete pre-bound BIDBH3, an excess of BADBH3 is required, despite the 5-fold greater affinity of BADBH3 for BCL-2 in solution. This finding suggests a conformational change takes place in either BCL-2 and/or a BH3 peptide upon binding. In contrast, BIDBH3 does not effectively displace BADBH3 from BCL-2. Testing the remaining peptides reveals that those peptides which cause cytochrome c release by themselves (BIDBH3 and BIMBH3) or those which enable cytochrome c release by counteracting BCL-2 (BADBH3 and BIKBH3) all bind to BCL-2 with affinities in the 50-500 nM range. BADBH3 and BIKBH3 demonstrate the ability to displace BIDBH3 from the BCL-2 protein (Table 1). The remaining peptides (NOXABH3, NOXABBH3, BCLXBH3, BIDBH3mut) which were unable to overcome BCL-2 inhibition did not bind detectably to BCL-2 or displace BIDBH3 from BCL-2 (Table 1). These results are consistent with the capacity of "sensitizing" BH3 domains (e.g. BADBH3 or BIKBH3) to displace "activating" BH3 domains (e.g. BIDBH3 or BIMBH3) from the pocket of anti-apoptotic BCL-2. Once free, "activating" BH3 domains by this model would trigger BAK oligomerization with subsequent cytochrome c release (FIG. 7C).

Figure 8:
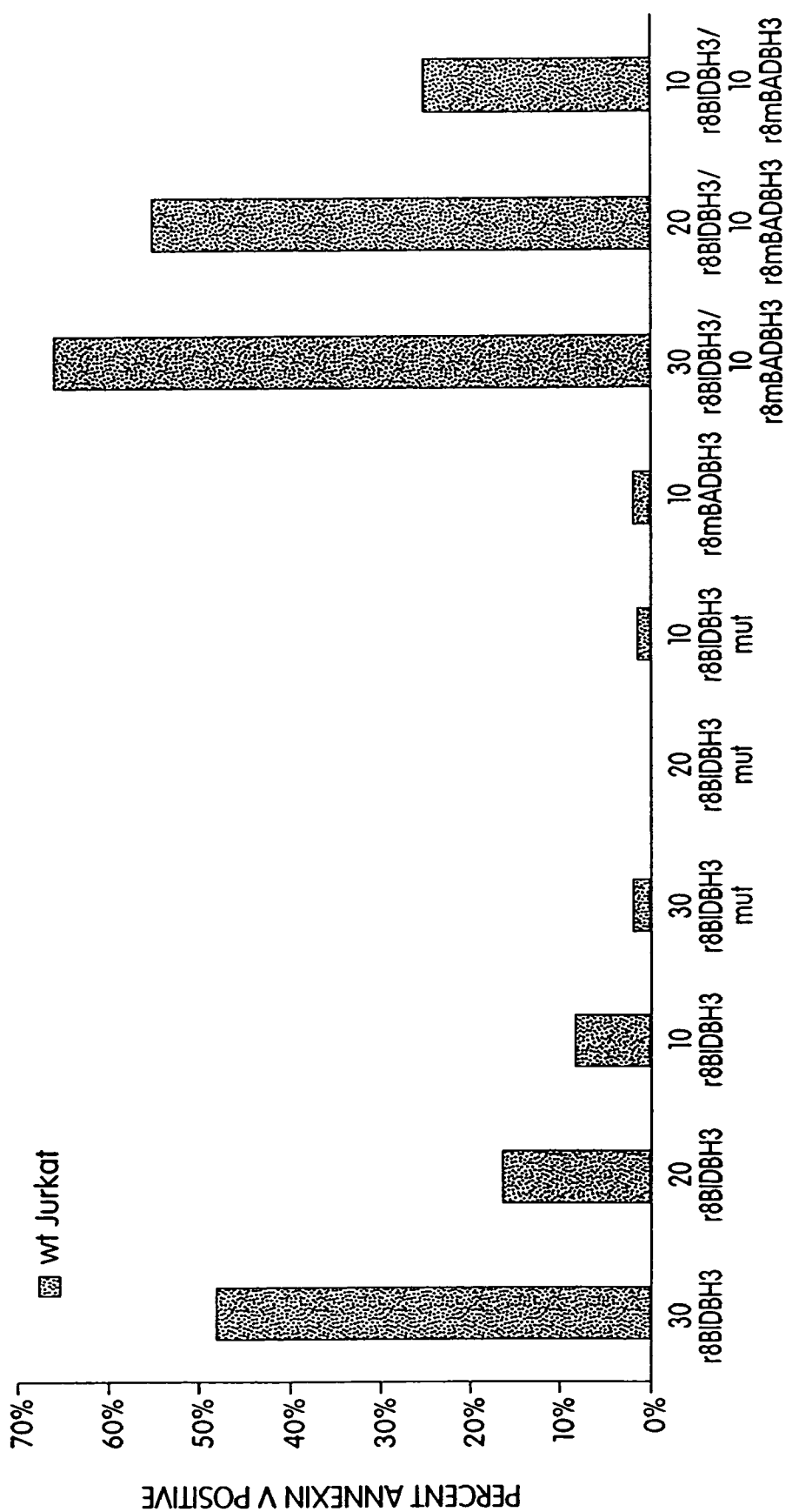
FIG. 8 is a bar chart showing r8BADBH3 sensitizes Jurkat cells to r8BIDBH3 killing.

Whether apoptosis of cancer cells could be triggered by transduction of such BH3 peptides was explored. Prior studies utilizing internalization moieties including decanoic acid, antennepedia (ANT) or HIV Tat have noted confounding issues of cellular and mitochondrial toxicity. For example, when various BH3 domains were linked to a Tat 11-mer both wt and mutant transduced peptides rapidly killed cells. Moreover, many conjugates did not appear to work through the genetic pathway as they displayed no inhibition by BCL-2 and readily killed Bax, Bak doubly deficient cells (not shown). Linking a polyarginine (8 aa) stretch to the BH3 peptides appears more promising. Polyarginine tags have been shown to facilitate the transport of peptides across the plasma membrane (Rothbard et al., 2000). r8BIDBH3 was capable of killing Jurkat leukemic cells, whereas r8BIDBH3mut was ineffective. Moreover, the addition of non-toxic 10YM r8BADBH3 was able to sensitize Jurkat cells to subliminal concentrations (10 µM) of r8BIDBH3 (FIG. 8). Both r8BIDBH3 and r8BADBH3 failed to kill Bax, Bak doubly-deficient cells. Thus, this appears to provide an initial proof of concept experiment that "sensitizing" and "activating" BH3 domains will also synergize in vivo to initiate apoptosis of cancer cells.

EXAMPLE 8

The use of synthetic peptides coupled with genetically defined mitochondria indicate that the BH3 peptide domain itself, excised from the context of an entire BH3-only molecule, can function as a specific death ligand. The activity of BH3 peptides supports a ligand/receptor model in which "BID-like" BH3 domains are sufficient to trigger allosteric conformational activation of BAX, BAK, their respective receptors. Activation by BIDBH3 peptide was qualitatively indistinguishable from the myrBID protein in that either requires BAK, results in BAK oligomerization followed by cytochrome c release, and can be bound and sequestered by BCL-2 with resultant protection of BAK. The synthetic peptides also indicate that BH3 regions are true domains rather than merely conserved sequence motifs, as the peptide domain itself has inherent functional activity. Comparison of various α-helical peptides from BH3-only proteins reveals evidence for 2 functional classes of BH3 domains. BID-like domains "activate" multidomain proapoptotic BAX, BAK. Whereas, BAD-like domains "sensitize" mitochondria for apoptosis by occupying the pocket of anti-apoptotic BCL-2. The latter displace BID-like domains which even at subliminal levels can now initiate cytochrome c release. This predicts that therapeutics which mimic a BH3 domain, whether they be peptidomimetics or small molecules, will be assignable to these functional classes and should be classified utilizing the genetic and molecular reagents defined here.

From a therapeutic vantage point, BAD-like "sensitizing" BH3 mimetics would possess several attractive characteristics. They might be predicted to reset susceptibility of cells protected by BCL-2 or BCLX$_L$, but would require a second apoptotic signal to initiate an "activating" BH3-only protein. This implies that as a single agent, "sensitizing" mimetics might prove non-toxic, especially to normal cells. The need for a second signal provides the opportunity to utilize cancer cell selective pathways that could also spare normal cells.

Evidence here for a "sensitizing" subset of BAD-like BH3 peptides provides an explanation for previous, apparent discrepancies concerning the mechanism of action of these proteins. Most BH3-only intact proteins including BAD, NOXA and BIK display a marked binding preference for anti-apoptotic members BCL-2, BCL-X$_L$ in interaction assays of yeast two-hybrid, pull down, or co-immunoprecipitation from detergent solubilized lysates (Boyd et al., 1995; Oda et al., 2000; Yang et al., 1995). Moreover, mutational analysis suggested that only when BAD was able to bind anti-apoptotic BCL-X$_L$ was it capable of promoting death (Kelekar and Thompson, 1998). Yet, BAD, NOXA and BIK all require the multidomain proapoptotic BAX, BAK proteins to kill as evidenced in Bax, Bak-doubly deficient cells (Cheng et al., 2001; Zong et al., 2001). The ability of BAD-like BH3 peptides to mediate a displacement reaction from the anti-apoptotic BCL-2 pocket provides a mechanism of action that would accommodate all observations. The cooperating protein displaced from anti-apoptotic pockets within intact cells would include, but not be restricted to, BID-like "activating" BH3-only members. While helping to resolve this issue, the analysis of the BIMBH3 peptide proved provocative. Prior interaction assays indicate that the intact BIM protein displays preferential binding to anti-apoptotic BCL-2, BCL-X$_L$ over proapoptotic BAX or BAK. Previous reports testing the capacity of intact BIM protein to release cytochrome c from mitochondria gave differing results (Li et al., 2001; Terradillos et al., 2002). Here, the isolated BIM BH3 domain when removed from the context of the entire protein scored as BID-like, capable of activating BAX, BAK. Several potential explanations can be envisioned. It is possible that the critical α-helical face of the BH3 domain that recognizes BAX, BAK may not be exposed in the intact BIM protein. Alternatively, it is also conceivable that the standard protein interaction assays used to measure binding may not reflect all of the conformational states that a native BIM molecule undergoes during cell death in-vivo.

The mechanistic pathway to cytochrome c release for BIDBH3 peptide appears similar to native myrBID complex, yet the efficiency of triggering varies greatly. Near total release of cytochrome c from mitochondria requires but 10 nM myrBID complex, but 10 µM BIDBH3 peptide. Myristoylation increases the efficiency of BID targeting to mitochondria and could conceivably help focus its location on the outer mitochondrial membrane (Lutter et al., 2001; Zha et al., 2000). It is also possible that an integrated myrp15BID protein may more effectively present the BH3 domain to the BAK pocket. Of note the sources of mitochondria vary in their response to individual BH3 domains. BIDBH3 is more potent than BIMBH3 for liver mitochondria, whereas BIMBH3 is more effective on the FL5.12 mitochondria. This may reflect the presence of BAX on FL5.12 but not liver mitochondria. The efficiency of oligomerization (FIG. 4) supports a preference of BIDBH3 for BAK and BIMBH3 for BAX. An hypothesis that BIMBH3 prefers BAX would be consistent with the finding that BIM functions upstream of BAX in neuronal cell death following NGF deprivation (Putcha et al., 2001). The binding affinity of individual BH3 domains for BCL-2 members varies considerably (Sattler et al., 1997) (FIG. 7) providing a measurement for selectivity. Assessment of BH3 peptides by circular dichroism indicates that α-helical content is not the sole determinant of differential binding affinity, nor for the ability to induce BAX, BAK oligomerization and cytochrome c release. The specificity noted suggests a model in which distinct BH3 domains have select multidomain partners which provides a rationale for the large number of both BH3-only and multidomain antiapoptotic members.

Whether the BH3 domains of multidomain members can initiate apoptosis is less certain. The BH3 domain isolated from BCL-$X_L$ studied here showed no activity, while BH3 peptides from BAX have generated mixed results. Addition of a BH3 peptide from BAK to a *Xenopus* cell free system induced release of cytochrome c and caspase activity, although the site of action was unknown (Cosulich et al., 1997). Addition of BAXBH3 to mammalian mitochondria has been reported to release cytochrome c without inducing permeability transition (Polster et al., 2001), consistent with the mechanistic pathway dissected here; whereas, others report BAXBH3 peptides which do induce permeability transition and loss of transmembrane potential as an explanation for cytochrome c release (Narita et al., 1998). This may be inherent to α-helices themselves or to hybrid proteins which can damage organelle membranes.

A substantial challenge for the future is to effectively transduce BH3 peptides or BH3 peptidomimetics into cells and assure that the induction of apoptosis is through the genetic pathway. Several studies (Holinger et al., 1999; Wang et al., 2000) including the initial polyarginine transduction approach presented here suggest this warrants further efforts. However, caution exists as a number of amphipathic α-helical peptides, especially if they are cationic, can be attracted to negatively charged membranes, including mitochondrial membranes where they can non-specifically disrupt the lipid matrix and membrane barrier function (Ellerby et al., 1999; Matsuzaki, 2001; Westerhoff et al., 1989). Others utilizing ANT-BH3BAD found toxicity was independent of the BCL-2 pathway and also killed yeast, which tolerate expression of the BH3-only proteins (Schimmer et al., 2001; Vieira et al., 2002). Alternative methods of internalization including receptor mediated pathways should also be considered for BH3 peptidomimetics. The work here provides a proof of concept that BH3 mimetics can be designed which initiate apoptosis correctly, at definable points in the genetic pathway. Moreover, it provides a paradigm and reagents to dissect the mechanism of action of future BH3 mimetics.

EXAMPLE 9

Screening for BH3-Mimetics Using a Mitochodrial Assay

Figure 9:
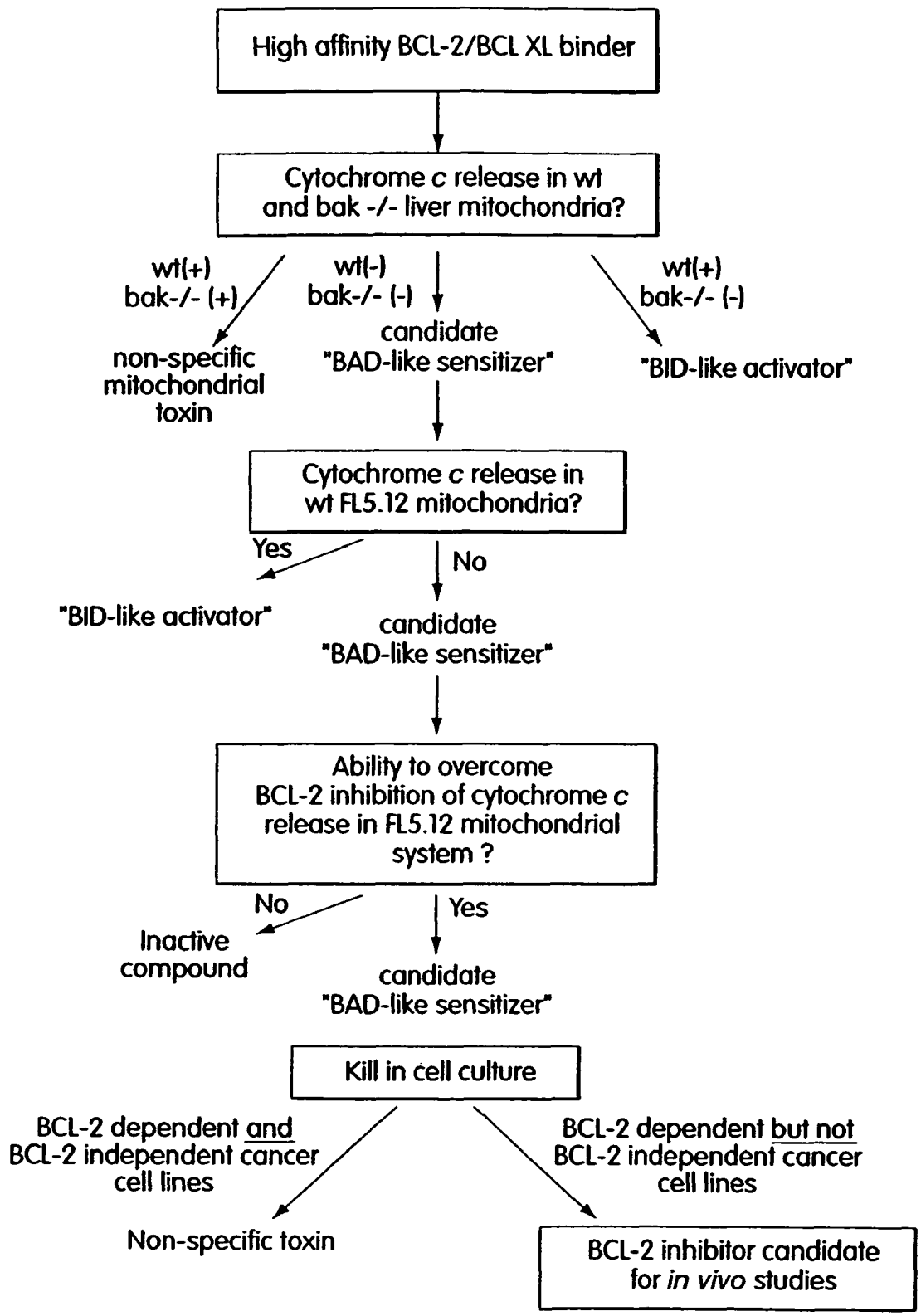
FIG. 9 is a schematic representation of a BH3-mimetic screening strategy.

BH3-mimetics, e.g., BAD-like or BID-like, are screened using a mitochondrial assay. (See, FIG. 9) Mitochondria from livers of mice that are either wild-type or Bak−/− are isolated. Isolated mitochondria are contacted with a test compound and cytochrome c release is determined. No cytochrome c release in either wt or Bak−/− mitochondria indicates the test compound is a "sensitizing", BAD-like mimetic. To further test this potential "sensitizing" BAD-like mimetic is added to subliminal concentration of a BID-like mimetic myrBID itself to determine if cytochrome c release is enhanced from BAK wt mitochondria. A BAD like mimetic is useful for example as a specific BCL-2/BCL-$X_L$ inhibitor. A compound that induces cytochrome c release in wt but not Bak−/− mitochondria indicates the compound is an "activating" BID-like mimetic. BADBH3 and myrBID are used as controls for sensitizing and activating compounds respectively.

Candidate sensitizing compounds are further characterized by isolating mitochondria from either wt or over expressing BCL-2 FL5.12 cells. Sensitizer compound do not induce cytochrome c release from wt F15.12 mitochondria, however sensitizer compounds do enable subliminal concentrations of myrBID or a BID-like mimetic to release cytochrome c from BCL-2 protected mitochondria.

A candidate sensitizing compound is further tested for its ability to kill BCL-2 dependent rather than BCL-2 independent cancer cells in culture.

EXAMPLE 10

Production and Characterization of BCL-2 Conditional Knockin Mouse

Using standard recombinant DNA technology, the tet-BCL-2 allele was targeted to the DNA methyltransferase 1 locus (FIG. 10). By crossing the new mouse line with the MMTV-tTA line (Jackson Labs) mice were generated which conditionally overexpresse BCL-2 in epithelial cells and in B-lineage lymphocytes. Administration of doxycycline successfully suppresses BCL-2 overexpression in these animals. When these mice are crossed with mice expressing myc in the B-lymphocyte lineage (Eμ-myc mice, Jackson Labs) mice which uniformly have B-cell lymphoblastic leukemia were obtained.

Figure 11:
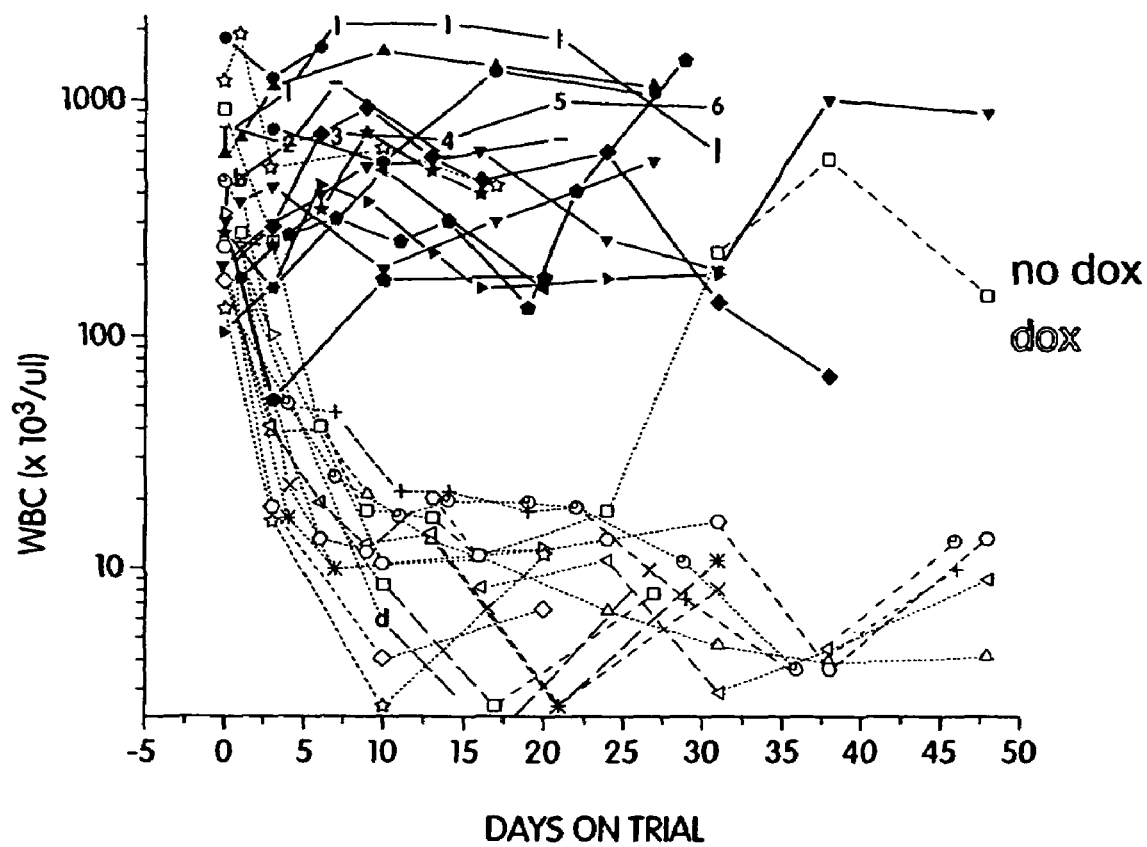
FIG. 11 is a bar chart showing that the loss of BCL-2 expression induced by doxycycline treatment induces a dramatic, 1-2 log decrease in WBC and a remission of the leukemia FIG. 12 are photographs of a Western Blot depicting the expression of hBcl-2 in the spleen.
Figure 12:
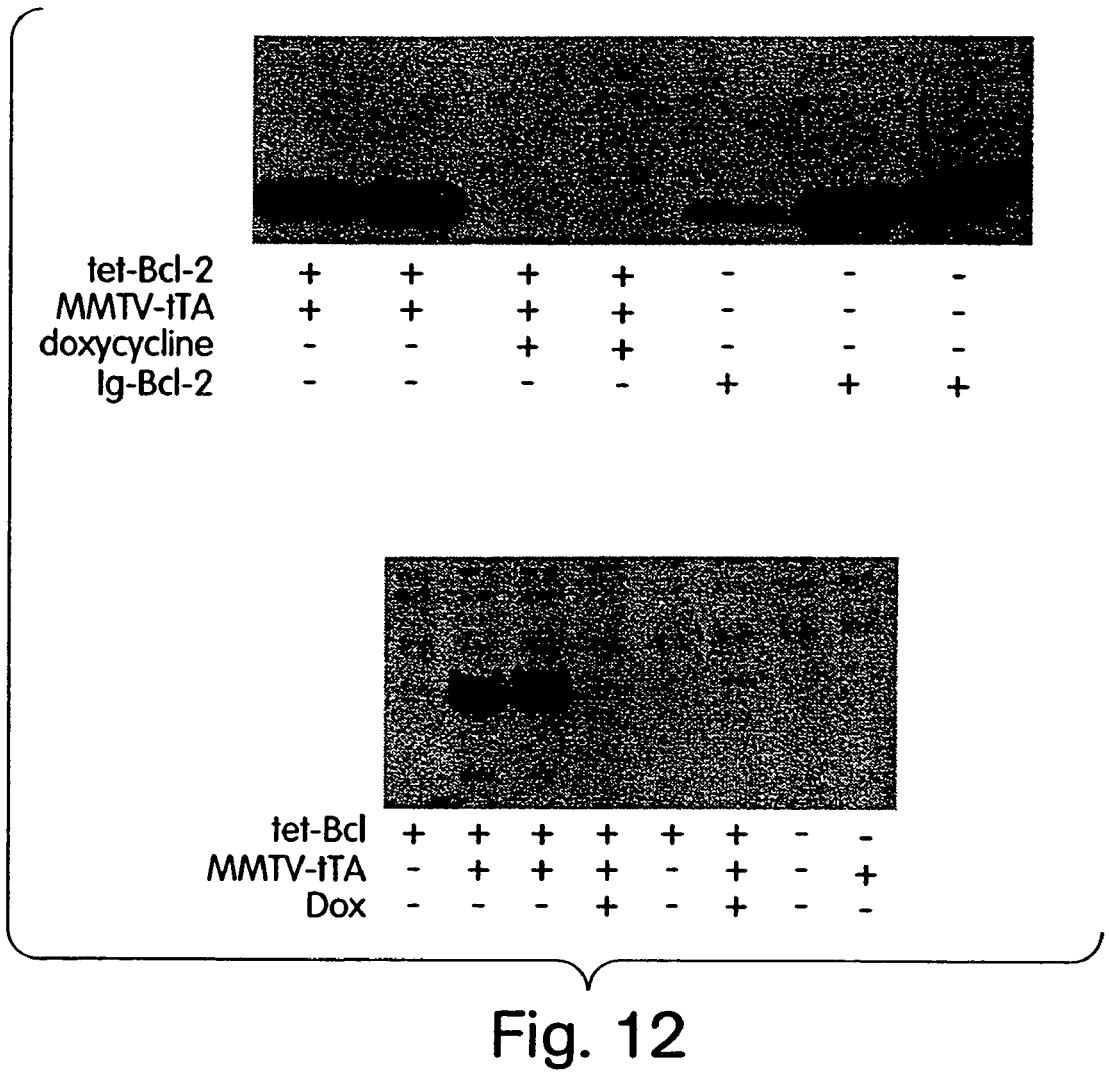
Figure 13:
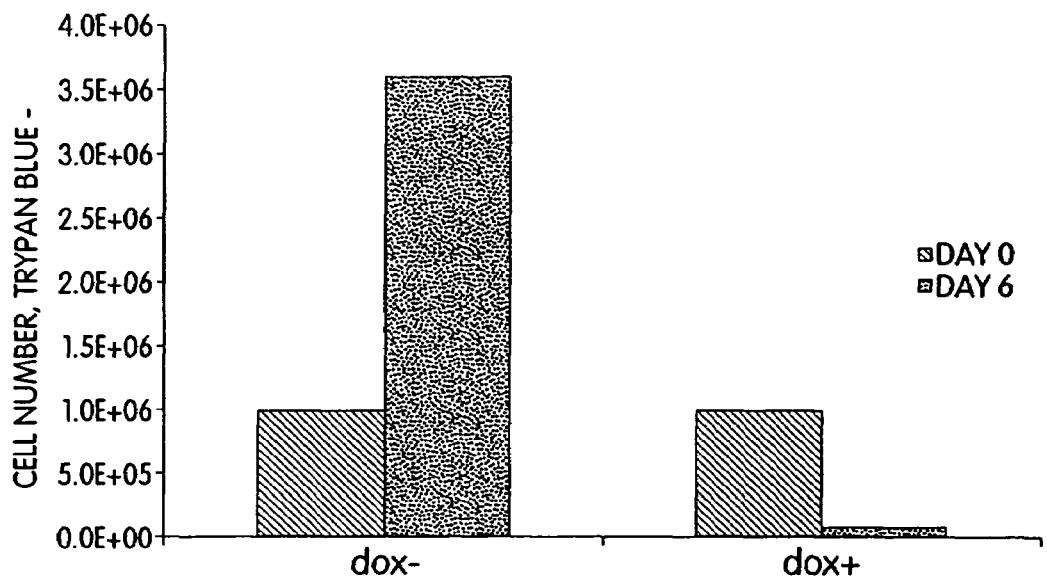
FIG. 13 is bar chart depicting the requirement of BCL-2 expression for leukemia cell survival.
Figure 14:
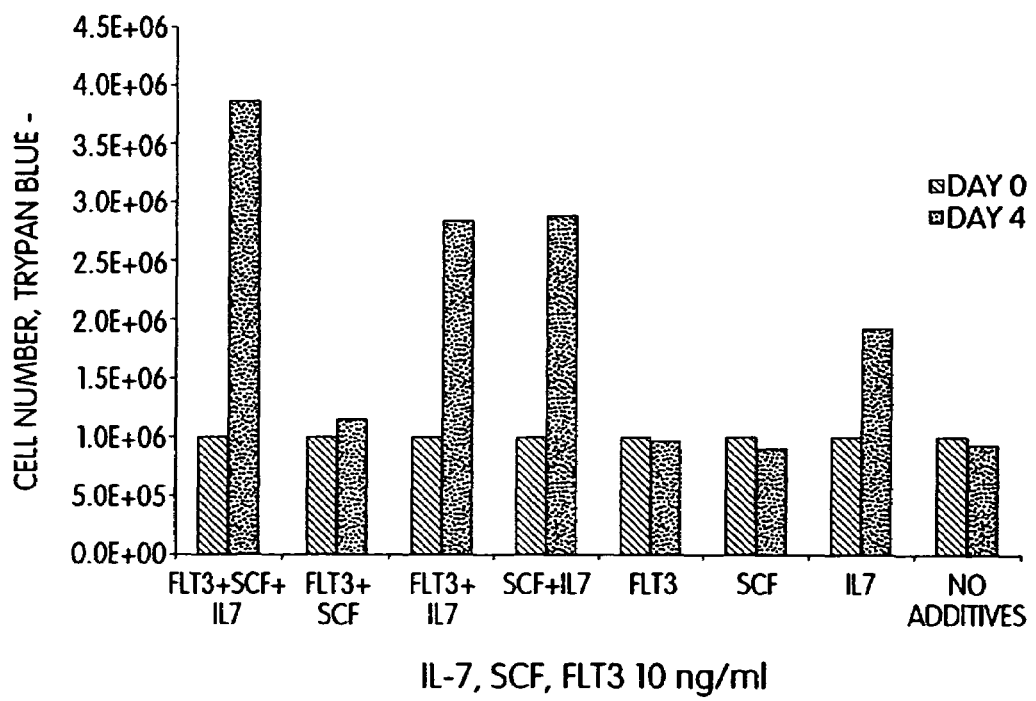
FIG. 14 is bar chart depicting the requirement of IL-7 for leukemia cell growth in culture.

To examine the effect of removing BCL-2 expression form the leukemia cells, the effects of doxycycline treatment in a cohort of 28 mice were examined. By genotype, each of the 28 mice contained the tet-BCL-2, the MMTV-tTA, and the Eμ-myc alleles. Phenotypically, each were found to have leukemia by blood smear, and a WBC in excess of 100,000/μl. At 4-5 weeks of age, half were treated with doxycycline (500 μg/ml) in drinking water, and half were left untreated. The WBC was measured by hemocytometer using 2 μl blood from tail which was lysed with 0.3% saponin and stained with Hoechst 33258. As shown in FIG. 11 that the loss of BCL-2 expression induced by doxycycline treatment induces a dramatic, 1-2 log decrease in WBC and a remission of the leukemia. These data provide strong support for the requirement of BCL-2 for tumor maintenance in this murine cancer model, and validates this model for future in vivo testing of candidate BCL-2 inhibitors.

EXAMPLE 11

Propagation of a Cell Lines Derived from the BCL-2 Conditional Knockin Mouse

A culture a cell line from the bone marrow of a triply transgenic, leukemic mouse was propagated. When BCL-2 transgene expression is eliminated by doxycycline treatment, the cell line dies. This BCL-2 dependent cancer cell line is useful for cellular testing of candidate BCL-2 inhibitors.

Furthermore, as a control for specificity of a putative BCL-2 antagonist, a cell line from B-cell malignancies which are not dependent on BCL-2 expression were generated. The tumors arose in triply transgenic mice that had not been maintained on doxycycline to abolish BCL-2 transgene expression. Cell from these mice were grown in culture in the absence of doxycycline. Turning off BCL-2 expression by administration of doxycycline did not induce cell death. These results demonstrate that these cell lines are useful in conjunction with the BCL-2 dependent cell line described above to assess the specificity of action of a putative BCL-2 antagonist. A specific BCL-2 antagonist is a compound that kills the BCL-2 dependent cell line but does not kill the BCL-2 independent cell line.

REFERENCES

Adams, J. M., and Cory, S. (1998). The Bcl-2 protein family: arbiters of cell survival. Science 281, 1322-1326.

Boyd, J. M., Gallo, G. J., Elangovan, B., Houghton, A. B., Malstrom, S., Avery, B. J., Ebb, R. G., Subramanian, T., Chittenden, T., Lutz, R. J., and et al. (1995). Bik, a novel death-inducing protein shares a distinct sequence motif with Bcl-2 family proteins and interacts with viral and cellular survival-promoting proteins. Oncogene 11, 1921-1928.

Cheng, E. H., Wei, M. C., Weiler, S., Flavell, R. A., Mak, T. W., Lindsten, T., and Korsmeyer, S. J. (2001). BCL-2, BCL-X(L) sequester BH3 domain-only molecules preventing BAX- and BAK-mediated mitochondrial apoptosis. Mol Cell 8, 705-711.

Chittenden, T., Flemington, C., Houghton, A. B., Ebb, R. G., Gallo, G. J., Elangovan, B., Chinnadurai, G., and Lutz, R. J. (1995). A conserved domain in Bak, distinct from BH1 and BH2, mediates cell death and protein binding functions. Embo J 14, 5589-5596.

Cosulich, S. C., Worrall, V., Hedge, P. J., Green, S., and Clarke, P. R. (1997). Regulation of apoptosis by BH3 domains in a cell-free system. Curr Biol 7, 913-920.

Ellerby, H. M., Arap, W., Ellerby, L. M., Kain, R., Andrusiak, R., R10, G. D., Krajewski, S., Lombardo, C. R., Rao, R., Ruoslahti, E., et al. (1999). Anti-cancer activity of targeted pro-apoptotic peptides. Nat Med 5, 1032-1038.

Eskes, R., Desagher, S., Antonsson, B., and Martinou, J. C. (2000). Bid induces the oligomerization and insertion of Bax into the outer mitochondrial membrane. Mol Cell Biol 20, 929-935.

Griffiths, G. J., Dubrez, L., Morgan, C. P., Jones, N. A., Whitehouse, J., Corfe, B. M., Dive, C., and Hickman, J. A. (1999). Cell damage-induced conformational changes of the pro-apoptotic protein Bak in vivo precede the onset of apoptosis. J Cell Biol 144, 903-914.

Gross, A., Jockel, J., Wei, M. C., and Korsmeyer, S. J. (1998). Enforced dimerization of BAX results in its translocation, mitochondrial dysfunction and apoptosis. Embo J 17, 3878-3885.

Holinger, E. P., Chittenden, T., and Lutz, R. J. (1999). Bak BH3 peptides antagonize Bcl-xL function and induce apoptosis through cytochrome c-independent activation of caspases. J Biol Chem 274, 13298-13304.

Kelekar, A., and Thompson, C. B. (1998). Bcl-2-family proteins: the role of the BH3 domain in apoptosis. Trends Cell Biol 8, 324-330.

Li, H., Zhu, H., Xu, C. J., and Yuan, J. (1998). Cleavage of BID by caspase 8 mediates the mitochondrial damage in the Fas pathway of apoptosis. Cell 94, 491-501.

Li, L. Y., Luo, X., and Wang, X. (2001). Endonuclease G is an apoptotic DNase when released from mitochondria. Nature 412, 95-99.

Luo, X., Budihardjo, I., Zou, H., Slaughter, C., and Wang, X. (1998). Bid, a Bcl2 interacting protein, mediates cytochrome c release from mitochondria in response to activation of cell surface death receptors. Cell 94, 481-490.

Lutter, M., Perkins, G. A., and Wang, X. (2001). The pro-apoptotic Bcl-2 family member tBid localizes to mitochondrial contact sites. BMC iCell Biol 2, 22.

Matsuzaki, K. (2001). Why and how are peptide-lipid interactions utilized for self defence? Biochem Soc Trans 29, 598-601.

Narita, M., Shimizu, S., Ito, T., Chittenden, T., Lutz, R. J., Matsuda, H., and Tsujimoto, Y. (1998). Bax interacts with the permeability transition pore to induce permeability transition and cytochrome c release in isolated mitochondria. Proc Natl Acad Sci USA 95, 14681-14686.

O'Connor, L., Strasser, A., O'Reilly, L. A., Hausmann, G., Adams, J. M., Cory, S., and Huang, D.C. (1998). Bim: a novel member of the Bcl-2 family that promotes apoptosis. Embo J 17, 384-395.

Oda, E., Ohki, R., Murasawa, H., Nemoto, J., Shibue, T., Yamashita, T., Tokino, T., Taniguchi, T., and Tanaka, N. (2000). Noxa, a BH3-only member of the Bcl-2 family and candidate mediator of p53-induced apoptosis. Science 288, 1053-1058.

Polster, B. M., Kinnally, K. W., and Fiskum, G. (2001). BH3 death domain peptide induces cell type-selective mitochondrial outer membrane permeability. J Biol Chem 276, 37887-37894.

Putcha, G. V., Moulder, K. L., Golden, J. P., Bouillet, P., Adams, J. A., Strasser, A., and Johnson, E. M. (2001). Induction of BIM, a proapoptotic BH3-only BCL-2 family member, is critical for neuronal apoptosis. Neuron 29, 615-628.

Rothbard, J. B., Garlington, S., Lin, Q., Kirschberg, T., Kreider, E., McGrane, P. L., Wender, P. A., and Khavari, P. A. (2000). Conjugation of arginine oligomers to cyclosporin A facilitates topical delivery and inhibition of inflammation. Nat Med 6, 1253-1257.

Sattler, M., Liang, H., Nettesheim, D., Meadows, R. P., Harlan, J. E., Eberstadt, M., Yoon, H. S., Shuker, S. B., Chang, B. S., Minn, A. J., et al. (1997). Structure of Bcl-xL-Bak peptide complex: recognition between regulators of apoptosis. Science 275, 983-986.

Schimmer, A. D., Hedley, D. W., Chow, S., Pham, N. A., Chakrabartty, A., Bouchard, D., Mak, T. W., Trus, M. R., and Mindeni, M. D. (2001). The BH3 domain of BAD fused to the Antennapedia peptide induces apoptosis via its alpha helical structure and independent of Bcl-2. Cell Death Differ 8, 725-733.

Terradillos, O., Montessuit, S., Huang, D.C., and Martinou, J. C. (2002). Direct addition of BimL to mitochondria does not lead to cytochrome c release. FEBS Lett 522, 29-34.

Vieira, H. L., Boya, P., Cohen, I., El Hamel, C., Haouzi, D., Druillenec, S., Belzacq, A. S., Brenner, C., Roques, B., and Kroemer, G. (2002). Cell permeable BH3-peptides overcome the cytoprotective effect of Bcl-2 and Bcl-X(L). Oncogene 21, 1963-1977.

Wang, J. L., Zhang, Z. J., Choksi, S., Shan, S., Lu, Z., Croce, C. M., Alnemri, E. S., Korngold, R., and Huang, Z. (2000). Cell permeable Bcl-2 binding peptides: a chemical approach to apoptosis induction in tumor cells. Cancer Res 60, 1498-1502.

Wang, K., Yin, X. M., Chao, D. T., Milliman, C. L., and Korsmeyer, S. J. (1996). BID: a novel BH3 domain-only death agonist. Genes Dev 10, 2859-2869.

Wei, M. C., Lindsten, T., Mootha, V. K., Weiler, S., Gross, A., Ashiya, M., Thompson, C. B., and Korsmeyer, S. J. (2000). tBID, a membrane-targeted death ligand, oligomerizes BAK to release cytochrome c. Genes Dev 14, 2060-2071.

Wei, M. C., Zong, W. X., Cheng, E. H., Lindsten, T., Panoutsakopoulou, V., Ross, A. J., Roth, K. A., MacGregor, G. R., Thompson, C. B., and Korsmeyer, S. J. (2001). Proapoptotic BAX and BAK: a requisite gateway to mitochondrial dysfunction and death. Science 292, 727-730.

Westerhoff, H. V., Juretic, D., Hendler, R. W., and Zasloff, M. (1989). Magainins and the disruption of membrane-linked free-energy transduction. Proc Natl Acad Sci USA 86, 6597-6601.

Wolter, K. G., Hsu, Y. T., Smith, C. L., Nechushtan, A., Xi, X. G., and Youle, R. J. (1997). Movement of Bax from the cytosol to mitochondria during apoptosis. J Cell Biol 139, 1281-1292.

Yang, E., Zha, J., Jockel, J., Boise, L. H., Thompson, C. B., and Korsmeyer, S. J. (1995). Bad, a heterodimeric partner for Bcl-XL and Bcl-2, displaces Bax and promotes cell death. Cell 80, 285-291.

Yang, J. T., Wu, C. S., and Martinez, H. M. (1986). Calculation of protein conformation from circular dichroism. Methods Enzymol 130, 208-269.

Zha, J., Harada, H., Osipov, K., Jockel, J., Waksman, G., and Korsmeyer, S. J. (1997). BH3 domain of BAD is required for heterodimerization with BCL-XL and pro-apoptotic activity. J Biol Chem 272, 24101-24104.

Zha, J., Weiler, S., Oh, K. J. Wei, M. C., and Korsmeyer, S. J. (2000). Posttranslational N-myristoylation of BID as a molecular switch for targeting mitochondria and apoptosis. Science 290, 1761-1765.

Zong, W. X., Lindsten, T., Ross, A. J., MacGregor, G. R., and Thompson, C. B. (2001). BH3-only proteins that bind pro-survival Bcl-2 family members fail to induce apoptosis in the absence of Bax and Bak. Genes Dev 15, 1481-1486.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated peptide of 50 amino acids or fewer comprising the amino acid sequence of SEQ ID NO: 6.

2. The peptide of claim 1, wherein said peptide binds or MCL-1.

3. An isolated peptide of SEQ ID NO: 6.

4. A chimeric peptide comprising a first domain and a second domain wherein said first domain comprises the amino acid sequence consisting of SEQ ID NO: 6 and said second domain comprises a translocation sequence which facilitates transport across a biological membrane.

5. The peptide of claim 4, wherein said translocation sequence is polyarginine.

6. A composition comprising a peptide of any one of claims 1-5 and a carrier.

* * * * *

SEQUENCE LISTING

```
<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 1

Glu Asp Ile Ile Arg Asn Ile Ala Arg His Leu Ala Gln Val Gly Asp
 1               5                  10                  15

Ser Met Asp Arg
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 2

Met Arg Pro Glu Ile Trp Ile Ala Gln Glu Leu Arg Arg Ile Gly Asp
 1               5                  10                  15

Glu Phe Asn Ala
            20

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 3

Leu Trp Ala Ala Gln Arg Tyr Gly Arg Glu Leu Arg Arg Met Ser Asp
 1               5                  10                  15

Glu Phe Glu Gly Ser Phe Lys Gly Leu
            20                  25

<210> SEQ ID NO 4
```

```
<211> LENGTH: 25
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 4

Asn Leu Trp Ala Ala Gln Arg Tyr Gly Arg Glu Leu Arg Arg Met Ser
 1               5                  10                  15

Asp Glu Phe Val Asp Ser Phe Lys Lys
            20                  25

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 5

Met Glu Gly Ser Asp Ala Leu Ala Leu Arg Leu Ala Cys Ile Gly Asp
 1               5                  10                  15

Glu Met Asp Val
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 6

Ala Glu Leu Pro Pro Glu Phe Ala Ala Gln Leu Arg Lys Ile Gly Asp
 1               5                  10                  15

Lys Val Tyr Cys
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 7

Pro Ala Asp Leu Lys Asp Glu Cys Ala Gln Leu Arg Arg Ile Gly Asp
 1               5                  10                  15

Lys Val Asn Leu
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 8

Val Ile Pro Met Ala Ala Val Lys Gln Ala Leu Arg Glu Ala Gly Asp
 1               5                  10                  15
```

Glu Phe Glu Leu
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 9

Glu Asp Ile Ile Arg Asn Ile Ala Arg His Ala Ala Gln Val Gly Ala
 1               5                  10                  15

Ser Met Asp Arg
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: VARIANT
<222> LOCATION: (1)..(6)
<223> OTHER INFORMATION: Wherein Xaa is any amino acid.
<220> FEATURE:
<221> NAME/KEY: VARIANT
<222> LOCATION: (9)..(10)
<223> OTHER INFORMATION: Wherein Xaa is any amino acid.
<220> FEATURE:
<221> NAME/KEY: VARIANT
<222> LOCATION: (12)..(14)
<223> OTHER INFORMATION: Wherein Xaa is any amino acid.
<220> FEATURE:
<221> NAME/KEY: VARIANT
<222> LOCATION: (17)..(20)
<223> OTHER INFORMATION: Wherein Xaa is any amino acid.

<400> SEQUENCE: 10

Xaa Xaa Xaa Xaa Xaa Xaa Ile Ala Xaa Xaa Leu Xaa Xaa Xaa Gly Asp
 1               5                  10                  15

Xaa Xaa Xaa Xaa
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: VARIANT
<222> LOCATION: (1)..(10)
<223> OTHER INFORMATION: Wherein Xaa is any amino acid.
<220> FEATURE:
<221> NAME/KEY: VARIANT
<222> LOCATION: (12)..(15)
<223> OTHER INFORMATION: Wherein Xaa is any amino acid.
<220> FEATURE:
<221> NAME/KEY: VARIANT
<222> LOCATION: (17)..(20)
<223> OTHER INFORMATION: Wherein Xaa is any amino acid.

```
<400> SEQUENCE: 11

Xaa Xaa Xaa Xaa Xaa Xaa Xaa Xaa Xaa Xaa Leu Xaa Xaa Xaa Xaa Asp
 1               5                  10                  15

Xaa Xaa Xaa Xaa
            20
```